United States Patent [19]

Brookes et al.

[11] 4,251,262

[45] Feb. 17, 1981

[54] 1-CARBAMOYL-1,2,4-TRIAZOLE HERBICIDAL AGENTS

[75] Inventors: Robert F. Brookes, Tollerton; David H. Godson, Chilwell; Douglas Greenwood, Nottingham; Margaret Tulley, Mapperley; Stanley B. Wakerley, Burton Joyce, all of England

[73] Assignee: The Boots Company Limited, Nottingham, England

[21] Appl. No.: 19,671

[22] Filed: Mar. 12, 1979

Related U.S. Application Data

[60] Division of Ser. No. 849,367, Nov. 7, 1977, Pat. No. 4,148,626, which is a division of Ser. No. 603,572, Aug. 11, 1975, Pat. No. 4,087,269, which is a division of Ser. No. 317,453, Dec. 21, 1972, Pat. No. 3,952,001, which is a continuation-in-part of Ser. No. 261,206, Jun. 9, 1972, abandoned, which is a continuation-in-part of Ser. No. 153,446, Jun. 15, 1971, abandoned.

[30] Foreign Application Priority Data

Jul. 1, 1970 [GB] United Kingdom ............... 31922/70
Mar. 31, 1971 [GB] United Kingdom ............... 8275/71
Dec. 31, 1971 [GB] United Kingdom ............... 61022/71
Dec. 31, 1971 [GB] United Kingdom ............... 61023/71

[51] Int. Cl.$^3$ .................... A01N 47/38; C07D 249/12
[52] U.S. Cl. ......................................... 71/92; 548/265
[58] Field of Search ...................... 260/308 R; 71/92; 548/265

[56] References Cited

U.S. PATENT DOCUMENTS 3,308,131  3/1967  McKusick ...................... 260/308 R

*Primary Examiner*—Alton D. Rollins
*Attorney, Agent, or Firm*—Lawrence Rosen

[57] ABSTRACT

Novel 1-carbamoyl-1,2,4-triazoles, processes for their production, and herbicidal compositions and methods are described. The compounds are particularly useful for the pre-weed emergence control of the graminaccous weeds crabgrass, barnyard grass, yellow foxtail and Johnson grass.

16 Claims, No Drawings

1-CARBAMOYL-1,2,4-TRIAZOLE HERBICIDAL AGENTS

This application is a divisional of application Ser. No. 849,367, filed Nov. 7, 1977, now U.S. Pat. No. 4,148,626 which is a divisional of application Ser. No. 603,572, filed Aug. 11, 1975, now U.S. Pat. No. 4,087,269, which is a divisional of application Ser. No. 317,453, filed Dec. 21, 1972, now U.S. Pat. No. 3,952,001, which is a continuation-in-part of copending application Ser. No. 261306, filed 9th June 1972, now abandoned, which is in turn a continuation-in-part of application Ser. No. 153446, filed 15th June 1971, now abandoned.

The disclosures of the above noted parent applications are incorporated herein by reference.

The invention relates to new chemical compounds with herbicidal activity. More particularly, this invention relates to new 1,8,4-triazolea, herbicidal compositions containing these compounds as active ingredients, and the use of these compounds to control weeds.

In U.S. Pat. No. 3,308,131 there is described a broad group of 1,2,4-triazoles of the isomeric general formulae

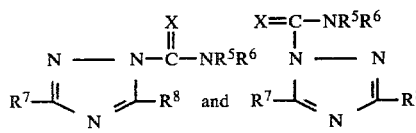

wherein X is oxygen or sulphur, $R^5$ and $R^6$ are aliphatic groups which together contain up to 14 carbon atoms and which may be joined to form a heterocyclic ring with the carbamoyl nitrogen atom, and $R^7$ and $R^8$, which together contain up to 14 carbon atoms, are free from aliphatic unsaturation and are selected from hydrogen, halogen, sulphonyl, mercapto, cyano, hydrocarbyl, halohydrocarbyl, nitrohydrocarbyl, hydrocarbyloxycarbonylhydrocarbyl, hydrocarbylsulphonyl, hydrocarbylmercapto, nitrohydrocarbylmercapto, halohydrocarbylmercapto, aminohydrocabylmercapto and hydrocarbyloxyhydrocarbyl. The compounds in this group are stated to be effective insecticides, particularly against miten and aphide. In addition, some of the compounds are stated to have analgesic properties.

We have now found that advantageous and valuable herbicidal properties are possessed by a relatively narrow group of new 1,2,4-triazoles, some of which compounds are encompassed by the broad group of 1,2,4-triazole defined above.

The new 1,2,4-triazoles provided by the present invention are 1-N,N-disubstituted-carbamoyl-1,2,4-tirazoles with a sulphur function in the 3-position, selected from the group consisting of (a) a compound of the formula

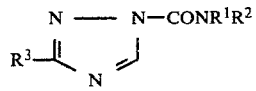

in which $R^3$ is alkythio containing 2-5 carbon atoms, alkylsulphinyl containing 3-5 carbon atoms, alkylsulphonyl containing 1-5 carbon atoms or alkenylthio containing 3 or 4 carbon atoms, $R^1$ is alkyl containing 2-6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being B 4-9 inclusive;

(b) a compound of the formula

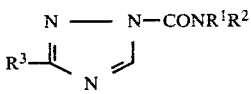

in which $R^3$ is alkylsulphonyl containing 1-5 carbon atoms, alkenyloxyalkylthio containing 4-6 carbon atoms, alkoxyalkylsulphinyl containing 2-6 carbon atoms, alkoxyalkylsulphonyl containing 2-6 carbon atoms, haloalkylsulphinyl containing 2-5 carbon atoms or haloalkylsulphonyl containing 1-5 carbon atoms, $R^1$ is alkyl containing 2-6 carbon atoms, allyl, 2-methylallyl, alkoxyalkyl containing 2-6 carbon aoms, alkenyloxyalkyl containing 4-6 carbon atoms, haloalkyl containing 2-6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2, 3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents; and (c) a compound of the formula

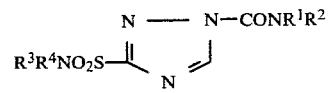

in which $R^1$ is alkyl containing 1 or 2 carbon atoms, allyl, 2-methylallyl, prop-2-ynyl, alkoxyalkyl containing 2-4 carbon atoms, haloalkyl containing 1-4 carbon atoms, 2-haloallyl, 2,3-dihaloallyl or cyclopropyl, $R^2$ is alkyl containing 2-8 carbon atoms, alkenyl containing 2-8 carbon atoms, alkenyloxyalkyl containing 4-8 carbon atoms (for example allyloxyalkyl or (2-methylallyl)oxyalkyl), haloalkyl containing 2-8 carbon atoms, 2-haloallyl, 2,3-dihaloallyl, cyclopropyl or cyclohexyl, $R^3$ is alkyl containing 1-4 carbon atoms, allyl, 2-methylallyl, prop-2-ynyl, alkoxyalkyl containing 2-4 carbon atoms, haloalkyl containing 1-4 carbon atoms, 2-haloallyl, 2,3-dihaloallyl, cyclopropyl or phenyl containing 1-3 halo substituents, $R^4$ is alkyl containing 1-8 carbon atoms, alkenyl containing 2-8 carbon atoms, alkoxyalkyl containing 2-8 carbon atoms, alkenyloxyalkyl containing 4-8 carbon atoms (for example allyloxyalkyl or (2-methylallyl)oxyalkyl), haloalkyl containing 1-8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionally containing 1-4 lower alkyl (preferably methyl) substituents, selected from morpholino, pyrrolidino, 1-piperidyl, hexamethyleneinino and heptamethyleneimino, provided that the total number of carbon atoms in $R^1$ and $R^2$ together is 3-9 inclusive, and when $R^3$ is a radical not containing a phenyl nucleus, the total number of carbon atoms in $R^3$ and $R^4$ together is 2-9 inclusive.

COMPOUNDS OF FORMULA II

The present invention provides new compounds of the general formula II in which $R^3$ is alkylsulphonyl containing 1-5 carbon atoms, alkenyloxyalkylthio containing 4-6 carbon atoms, alkoxyalkylsulphinyl containing 2–6 carbon atoms, alkoxyalkylsulphonyl containing 2–6 carbon atoms, haloalkylsulphinyl containing 2–5 carbon atoms or haloalkylsulphonyl containing 1–5 carbon atoms, $R^1$ is alkyl containing 2–6 carbon atoms, allyl, 2-methylallyl, alkoxyalky containing 2–6 carbon atoms, alkenyloxyalkyl containing 4–6 carbon atoms, haloalkyl containing 2–6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2, 3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

Preferably any alkoxy or halo substituent in an alkoxyalkyl or haloalkyl radical is attached in a position other than the alpha position, i.e. is attached to a carbon atom other than that which is attached to the nitrogen atom of the carbamoyl group $CONR^1R^2$ or the sulphur atom of the group $R^3$. Under these circumstances, when $R^3$ is alkoxyalkylsulphinyl or alkoxyalkylsulphonyl, it contains 3–6 carbon atoms, when $R^3$ is halcalkylsulphonyl it contains 2–5 carbon atoms, when $R^3$ is alkenyloxyalkylthio it contains 5 or 6 carbon atoms, when $R^1$ is alkoxyalkyl it contains 3–6 carbon atoms, when $R^1$ is alkenyloxyalkyl it contains 5 or 6 carbon atoms, and when $R^2$ is alkoxyalkyl it contains 3 or 4 carbon atoms. An alkenyloxyalkyl radical is, for example, allyloxyalkyl or (2-methylallyl)oxyalkyl.

The term "halo" includes chloro, bromo and fluoro and is preferably chlor or bromo, especially chloro. The term "alkoxy" includes alkoxy radicals with 1, 2, 3 or 4 carbon atoms, for example methoxy, ethoxy, propoxy, isopropoxy, n-butoxy and isobutoxy.

The alkyl, alkenyl, alkoxyalkyl or haloalkyl radical in the group $R^3$ may have a straight or branched chain, and is preferably a primary or secondary radical. The alkoxyalkyl radical in $R^3$ may contain 2, 3, 4, 5 or 6 carbon atoms and may be, for example, 2-methoxyethyl. 2-ethoxyethyl, 2-propoxyethyl, 2-n-butoxyethyl, 3-methoxypropyl, 3-ethoxypropyl, 2-methoxypropyl or 2-ethoxypropyl. The haloalkyl radical in $R^3$ may contain 2, 3,4 or 5 carbon atoms and may be, for example, 2-chlorethyl, 2-bromoethyl, 2-fluoroethyl, 3-chloropropyl, 3-bromopropyl, 4-chlorobutyl, 4-bromobutyl or 5-chloropentyl.

Values of $R^3$ include, for example, B 2-methoxyethylsulphinyl, 2-ethoxyethylsulphinyl, 2-propoxyethylsulphinyl, 2-n-butoxyethylsulphinyl, 3-methoxypropylsulphinyl, 3-ethoxypropylsulphinyl, 2-methoxypropylsulphinyl, 2-ethoxypropylsulphinyl, 2-chloroethylsulphinyl, 2-chloroethylsulphonyl, 2-bromoethylsulphinyl, 2-bromoethylsulphonyl, 3-chloropropylsulphinyl, 3-chloropropylsulphonyl, 4-chlorobutylsulphinyl, 4-chlorobutylsulphonyl, 2-chloroallylsulphinyl, 2-chloroallylsulphonyl, 2,3-dichloroallylsulphinyl,m 2,3-dichloroallylsulphonyl, 2-allyloxyethylthio and 3-allyloxypropylthio.

$R^3$ is preferably alkylsulphonyl or alkoxyalkylsulphonyl, such as for example, methylsulphonyl, ethylsulphonyl, propylsulphonyl, isopropylsulphonyl, n-butylsulphonyl, isobutylsulphonyl, sec.butylsulphonyl, 2-methoxyethylsulphonyl, 2-ethoxyethylsulphonyl, 2-propoxyethylsulphonyl, 2-n-butoxyethylsulphonyl, 3-methoxypropylsulphonyl, 3-ethoxypropylsulphonyl, 2-methoxypropylsulphonyl, 2-ethoxypropylsulphonyl, 1-methyl-2-propoxyethylsulphonyl. Especially suitable groups are alkylsulphonyl containing 2–4 carbon atoms, and alkoxyalkylsulphonyl containing 3 to 5 carbon atoms.

The radicals $R^1$ and $R^2$ may be straight or branched chain radicals, and are preferably primary or secondary radicals. Typical values of $R^1$ include, for example, ethyl, propyl, isopropyl, n-butyl, isobutyl, sec.butyl, n-pentyl, isopentyl, allyl, methoxymethyl, 2-methoxyethyl, 2-ethoxyethyl, 2-propoxyethyl, 2-n-butoxyethyl, 3-methoxypropyl, 3-ethoxypropyl, 2-allyloxyethyl, 3-allyloxypropyl, 2-methoxypropyl, 2-ethoxypropyl, 2-chloroethyl, 2-bromoethyl, 2-fluoroethyl, 3-chloropropyl, 3-bromopropyl, 4-chlorobutyl, 4-bromobutyl, 5-chloropentyl, 6-chlorohexyl, B 2-chloroallyl, 2-bromoallyl, 2,3-dichloroallyl and 2,3-dibromoallyl. Typical values of $R^2$ includes, for example, ethyl, propyl, isopropyl, allyl, 2-methylallyl, prop-2-ynyl, 2-methoxyethyl, 2-ethoxyethyl, 2-chloroethyl, 2-bromoethyl, 3-chloropropyl, 3-bromopropyl, 2-chloroallyl, 2-bromoallyl, 2,3-dichloroallyl, 2,3-dibromoallyl and cyclopropyl.

Typical values of the carbamoyl radical —$CONR^1R^2$ include, for example, dialkylcarbamoyl wherein the alkyl radicals are the same or different [for example diethylcarbamoyl, dipropylcarbamoyl, N-ethyl-N-propylcarbamoyl, N-butyl-N-ethylcarbamoyl, N-ethyl-N-hexylcarbamoyl, N-propyl-N-isopropylcarbamoyl, N-propyl-N-sec.butylcarbamoyl], diallylcarbamoyl, N-propyl-N-prop-2-ynylcarbamoyl, N-allyl-N-alkylcarbamoyl wherein the alkyl radical contains 2–6 carbon atoms [for example N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl, N-allyl-N-isopentylcarbamoyl, N-allyl-N-n-hexylcarbamoyl], N-allyl-N-(2-methoxyethyl)carbamoyl, N-allyl-N-(2-ethoxy ethyl)carbamoyl and N-allyl-N-(2-chloroethyl)carbamoyl, N-alkyl-N-methoxymethylcarbamoyl wherein the alkyl radical contains 2–6 carbon atoms [for example N-propyl-N-methoxymethylcarbamoyl], N-alkyl-N-(2-methoxyethyl)carbamoyl wherein the alkyl radical contains 2–6 carbon atoms [for example N-ethyl-N(2-methoxyethyl)carbamoyl, N-propyl-N-(2-methoxyethyl)carbamoyl and N-butyl-N-(2-methoxyethyl)carbamoyl]-N-alkyl-N-(2-ethoxyethyl)-carbamoyl wherein the alkyl radical contains 2–6 carbon atoms [for example N-ethyl-N-(2-ethoxyethyl)carbamoyl and N-propyl-N-(2-ethoxyethyl)carbamoyl], N-alkyl-N-(3-methoxypropyl)carbamoyl wherein the alkyl radical contains 2–6 carbon atoms, N-alkyl-N-(2-propoxyethyl)carbamoyl wherein the alkyl radical contains 2 or 3 carbon atoms, N-alkyl-N-(2-isopropoxyethyl)carbamoyl wherein the alkyl radical contains 2 or 3 carbon atoms, N-alkyl-N-(2-chloroallyl)carbamoyl wherein the alkyl radical contains 2–6 carbon atoms [for example N-propyl-N-(2-chloroallyl)-carbamoyl], N-alkyl-N-(2,3-dichloroallyl)carbamoyl wherein the alkyl radical contains 2–6 carbon atoms and N-alkyl-N-(2-chloroethyl)carbamoyl wherein the alkyl radical contains 2–6 carbon atoms.

When the compound of formula II contains an alkoxy substituent, $R^3$ is suitably alkylsulphonyl containing 2–4 carbon atoms or alkoxyalkylsulphonyl containing 3–5 carbon atoms. The carbamoyl group $CONR^1R^2$ is suitably dialkylcarbamoyl, N-alkyl-N-allylcarbamoyl, diallylcarbamoyl, N-alkyl-N-propynylcarbamoyl, N-alkyl-N-alkoxyalkylcarbamoyl, or N-allyl-N-alkoxyalkylcarbamoyl.

Preferred compounds of formula II having one or more alkoxy substituents are those in which:

(a) $R^3$ is alkylsulphonyl, the alkyl group containing 2, 3 or 4 carbon atoms, and the carbamoyl group $CONR^1R^2$ is N-alkyl-N-alkoxyalkylcarbamoyl or N-allyl-N-alkoxyalkylcarbamoyl, the alkyl group containing 2, 3 or 4 carbon atoms and the alkoxyalkyl groups containing 3 to 4 carbon atoms, especially 2-methoxethyl, 2-methoxypropyl or 2-ethoxyethyl, and (b) $R^3$ is alkoxyalkylsulphonyl, the alkoxyalkyl group containing 3 to 5 carbon atoms, especially 2-methoxyethyl, 3-methoxypropyl, 2-ethoxyethyl, 2-propoxyethyl, 2-isopropoxyethyl, and the carbamoyl group $CONR^1R^2$ is diallylcarbamoyl, N-alkyl-N-allyl-carbamoyl, N-alkyl-N-propynylcarbamoyl or dialkylcarbamoyl, the alkyl groups containing 2, 3 or 4 carbon atoms.

When the compound of formula II contains a halo atom a preferred group of compounds is one in which $R^3$ is alkylsulphonyl containing 2 or 3 carbon atoms or alkoxyalkylsulphonyl containing 3 to 5 carbon atoms. Preferably the carbamoyl group $CONR^1R^2$ is N-alkyl-N-(2-haloallyl)carbamoyl in which the alkyl group contains 2–4 carbon atoms and the halo atom is chlorine.

When $R^2$ is cyclopropyl a preferred group of compounds is one in which $R^3$ is alkylsulphonyl containing 2–4 carbon atoms, or alkoxyalkylsulphonyl containing 3–5 carbon atoms. Preferably the carbamoyl group $CONR^1R^2$ is N-cyclopropyl-N-alkylcarbamoyl in which the alkyl group contains 2, 3 or 4 carbon atoms.

The present invention also provides herbicidal compositions which comprise as an active ingredient a compound of the hereinbefore defined general formula II in association with a diluent or carrier. The diluent or carrier may be solid or liquid, optionally in association with a surface-active agent, for example a dispersing agent, emulsifying agent or wetting agent.

According to a further feature of the present invention there is provided a method for the pre-weed emergence control of graminaceous weeds which comprises applying to the locus of the weeds, for example the soil, a compound of the general formula II. A particular embodiment of this feature is a method for the selective pre-weed emergence control of graminaceous weeds such as barnyard grass, crabgrass, yellow foxtail and Johnson grass in a crop area which comprises applying to the crop area a compound of the general formula II at an application rate sufficient to control the weeds but substantially non-phytotoxic to the crop.

We have found that the triazole compounds of formulae I, II and III have valuable herbicidal properties against graminaceous weeds. For example, the compounds possess a high level of pre-weed emergence herbicidal activity against the graminaceous weeds crabgrass (*Dimitaria sanguinalis*), barnyard grass (*Echinochlea crussalli*), yellow foxtail (*Setaria lutescens*) and Johnson grass (*Sorghum halerense*). Furthermore, detailed trials in the glasshouse have shown that the compounds give a pre-weed emergence control of each of these weeds at application rates that cause no significant phytotoxic effect on the crops cotton, soyabean, peanut and maize when the compounds are applied prior to the emergence of these crops. Accordingly the compounds of the present invention can be used for the selective pre-emergence control of all of these weeds in these crops. This is an important advantage, since crabgrass, barnyard grass, yellow foxtail and Johnson grass are all important weeds in cotton, soyabean, peanut and maize and often occur together in these crops.

We have found that the compounds of the present invention have superior herbicidal properties to a variety of closely related 1,2,4-triazoles within the hereinbefore defined broad group of compounds described in U.S. Pat. No. 3,308,131, including a representative selection of the compounds specifically exemplified in that patent specification. Detailed trials in the glasshouse have demonstrated that, in contrast to the compounds of the present invention. these closely related compounds do not possess both the above-described high level of pre-weed emergence herbicidal activity and the above-described ability to control selectively all four of the weeds crabgrass, barnyard grass, yellow foxtail and Johnson grass in cotton, soyabean, peanut and maize.

The compositions of the present invention include not only compositions in a suitable form for application but also concentrated primary compositions which may be supplied to the user and which require dilution with a suitable quantity of water or other diluent before application.

Typical compositions falling within the present invention include the following:

(a) Dispersions and dispersible preparations

As dispersions, the compositions comprise essentially a triazole compound of the general formula I, II or III dispersed in an aqueous medium. It is convenient to supply the consumer with a primary composition which may be diluted with water to form a dispersion having the desired concentration; the primary composition may be in any one of the following forms. It may be provided as a dispersible solution which comprises a compound of the general formula I, II or III dissolved in a water-miscible solvent with the addition of a dispersing agent. Alternatively it may be provided as a dispersible powder which comprises a compound of the general formula I, II or III and a dispersing agent. A further alternative comprises a compound of the general formula I, II or III in the form of a finely ground powder in association with a dispersing agent and intimately mixed with water to give a paste or cream. This paste or cream may if desired be added to an emulsion of oil in water to give a dispersion of active ingredient in an aqueous oil emulsion.

(b) Emulsions and emulsifiable preparations

Emulsions comprise essentially a triazole compound of the general formula I, II or III dissolved in a water-immiscible solvent which is formed into an emulsion with water in the presence of an emulsifying agent. An emulsion of the desired concentration may be formed from a primary composition of the following types. A concentrated stock emulsion may be supplied comprising a compound of the general formula I, II or III in combination with an emulsifying agent, water and a water-immiscible solvent. Alternatively there may be supplied an emulsifiable concentrate comprising a solution of a compound of the general formula I, II or III in a water-immiscible solvent containing an emulsifying agent.

(c) Dusting powders

A dusting powder comprises a triazole compound of the general formula I, II or III intimately mixed and ground with a solid pulverulent diluent, for example kaolin.

(d) Granular solids

These may comprise a compound of the general formula I, II or III associated with similar diluents to those which may be employed in dusting powders, but the mixture is granulated by known methods. Alternatively they may comprise the active ingredient absorbed or adsorbed on a pre-formed granular diluent for example fullers earth, attapulgite and limestone grit.

In addition to the ingredients already mentioned, the compositions of the invention may also contain other substances conventionally used in the art, the function of which may be to improve the ease of handling of the compositions or to improve their utility. For example an inert diluent such as kaolin may be included in dispersible powders in order to facilitate grinding and to provide sufficient bulk for mixing with water. As a further example, the compositions intended for dilution with water prior to application may also contain a wetting agent in order to obtain rapid wetting-out of the materials and to ensure satisfactory coverage of the soil. Also when dusts are prepared, a lubricant such as magnesium stearate may be added to the mixture to promote both easier mixing of the components and to ensure that the final product has free-flowing properties.

The compositions hereinbefore described wherein the active ingredients are present in solid form, for example dusting powders and dispersible powders, should preferably contain the compound of the general formula I, II or III in the form of very fine particles; the majority of the particles, of the order of at least 95%, should be less than $50\mu$, with about 75% of them being $5-20\mu$. The adjuvants conventionally used in such compositions are generally of this particle size or smaller. The compositions can be prepared by means of conventional grinding equipment such as a hammer mill.

The concentration of compound of the general formula I, II or III in the primary compositions which may be provided for the preparation of any of the forms in which the compositions of the invention may be used may vary widely and may be, for example, 2-95% w/w of the composition. It will be appreciated that this concentration will be influenced by the nature of the primary composition and the physical properties of its ingredients.

The concentration of the compound of general formula I, II or III in the compositions for application to control weeds should be at least 0.001% w/w, preferably 0.05-10% w/w.

In addition to a compound of the general formula I, II or III, the compositions of the present invention may contain one or more additional active ingredients, for example one or more insecticides, nematocides, or additional herbicides. Such an additional herbicide may be, for example, a substituted urea, for example diuron or monuron; a triazine, for example simazine or atrazine; a substituted acetanilide, for example propachlor; a nitrophenyl ether, for example nitrofen; a carbamate, for example chlorpropham; or a thiolcarbamate, for example EPTC or tri-allate.

The invention includes a method for the pre-weed emergence control of graminaceous weeds which comprises applying to the locus of the weeds, for example the soil, a triazole compound of the formula I, II or III. This method may be used subsequent to the emergence of the crop, for example for the pre-weed emergence control of graminaceous weeds such as barnyard grass in seeded or transplanted rice, but is often used prior to the emergence of the crop, as is usually the case with the control of crabgrass, barnyard grass, yellow foxtail and Johnson grass in cotton, soyabean, peanut and maize. When the method is used prior to the emergence of the crop, it is convenient to apply the compounds of the invention to the soil in which the crop is sown at or just prior to the time of sowing. Thus, for example, the compounds of the invention may be incorporated into the top layer of soil as part of a sowing procedure.

For the control of graminaceous weeds, the compounds of the invention are generally used at an application rate of 0.05-50 lb./acre, preferably 0.1-20 lb./acre. Selective pre-weed emergence control of weeds may be achieved in many instances at an application rate within the range 0.1-10 lb./acre.

The selective pre-weed emergence herbicidal activity of the compounds of the present invention is demonstrated by the results obtained in detailed trials carried out in the glasshouse. In these trials, trays of soil were sown with seeds of various weeds and crops, and then immediately sprayed with aqueous suspensions of the compounds under test at logarithmically reducing application rates of test compound within the range 8-1/32 lb./acre. Seeded trays of soil receiving no chemical treatment were used as controls. The weeds used were crabgrass (CG), barnyard grass (BG), yellow foxtail (YF) and Johnson grass (JG). The crops used were cotton (CO), soyabean (SB), maize (M) and peanut (P).

In the case of the weeds, the minimum application rate was recorded at which control of the weeds was achieved, as shown by emergent seedlings that were severely and irrecoverably stunted. In the case of the crops, the minimum application rate was recorded at which a phytotomic effect was observed on the emergent seedlings. In some cases no phytotoxic effect on a crop was observed at the maximum application rate of test compound of 8 lb./acre, and this result was recorded as ">8". The results obtained with various compounds within the general formulae I, II and III are shown in the following Tables. In these Tables, the following abbreviations are used:

TABLE 1

| Compound (II) | | Minimum rate (lb./acre) | | | | | | | |
|---|---|---|---|---|---|---|---|---|---|
| | | Control | | | | Phytotoxicity | | | |
| R³ | NR¹R² | CG | BG | YF | JG | M | CO | SB | P |
| S(CH₂)₂Oallyl | NEt₂ | ½ | ½ | ½ | ½ | >8 | >8 | >8 | >8 |
| SO₂(CH₂)₂OEt | N(Et)Bu | 1/32 | 1/32 | 1/32 | 1/32 | ½ | 2 | 4 | >8 |
| SO₂(CH₂)₂OEt | N(allyl)Et | 1/32 | 1/32 | 1/32 | 1/32 | ½ | 1 | 2 | >8 |
| SO₂(CH₂)₂OEt | N(allyl)Pr | 1/32 | 1/32 | 1/32 | 1/32 | 1 | 1 | 2 | >8 |
| SO₂(CH₂)₂OEt | N(Pr)(prop-2-ynyl) | 1/16 | 1/32 | 1/16 | 1/32 | >8 | >8 | >8 | >8 |
| SO₂(CH₂)₂OPr | NEt₂ | ½ | ½ | 1/16 | 1/16 | ½ | 4 | >8 | >8 |
| SO₂(CH₂)₃OEt | NEt₂ | 1/16 | 1/16 | 1/16 | ½ | 2 | 2 | 4 | 8 |

TABLE 1-continued

| Compound (II) | | Minimum rate (lb./acre) | | | | | | | |
|---|---|---|---|---|---|---|---|---|---|
| | | Control | | | | Phytotoxicity | | | |
| $R^3$ | $NR^1R^2$ | CG | BG | YF | JG | M | CO | SB | P |
| $SO_2Et$ | N(Et)(CH$_2$)$_2$OMe | 1/16 | 1/16 | ⅛ | ¼ | 1 | 4 | >8 | >8 |
| $SO_2$i-Pr | N(Et)(CH$_2$)$_2$OMe | ¼ | ½ | ½ | ½ | 2 | >8 | >8 | >8 |
| $SO_2Bu$ | N(Et)(CH$_2$)$_2$OMe | 1/16 | ⅛ | ⅛ | ⅛ | ½ | >8 | >8 | >8 |
| $SO_2$i-Bu | N(Et)(CH$_2$)$_2$OMe | 1/16 | 1/16 | 1/32 | 1/32 | ½ | 2 | 2 | >8 |
| $SO_2Et$ | N(Et)(CH$_2$)$_2$OEt | 1/16 | 1/16 | 1/32 | 1/32 | 4 | >8 | >8 | >8 |
| $SO_2Pr$ | N(ET)(CH$_2$)$_2$OEt | 1/16 | ⅛ | ⅛ | 1/32 | 4 | >8 | >8 | 4 |
| $SO_2$i-Pr | N(Et)(CH$_2$)$_2$OEt | 1/16 | ¼ | ⅛ | ½ | >8 | >8 | 4 | >8 |
| $SO_2Bu$ | N(Et)(CH$_2$)$_2$OEt | ¼ | ¼ | ¼ | ¼ | >8 | >8 | >8 | >8 |
| $SO_2Et$ | N(Et)(CH$_2$)$_2$OMe | ⅛ | ¼ | ¼ | ¼ | 2 | >8 | >8 | >8 |
| $SO_2$i-Pr | N(Pr)(CH$_2$)$_2$OMe | ⅛ | ¼ | ¼ | ½ | 2 | >8 | 4 | >8 |
| $SO_2Bu$ | N(Pr)(CH$_2$)$_2$OMe | 1/16 | 1/16 | 1/16 | ¼ | 4 | 4 | >8 | >8 |
| $SO_2$i-Bu | N(Pr)(CH$_2$)$_2$OMe | 1/16 | 1/16 | ⅛ | ½ | 4 | >8 | >8 | >8 |
| $SO_2Et$ | N(Pr)(CH$_2$)$_2$OEt | ⅛ | ⅛ | ¼ | ¼ | 4 | >8 | 4 | >8 |
| $SO_2Pr$ | N(Pr)(CH$_2$)$_2$OEt | ¼ | 1 | ¼ | ½ | >8 | >8 | >8 | >8 |
| $SO_2Bu$ | N(Pr)(CH$_2$)$_2$OEt | 1/16 | ½ | ⅛ | ⅛ | 2 | >8 | >8 | >8 |
| $SO_2$i-Bu | N(Pr)(CH$_2$)$_2$OEt | ¼ | ½ | ½ | ½ | 2 | >8 | >8 | >8 |
| $SO_2Et$ | N(Pr)(Bu)(CH$_2$)$_2$OMe | 1/32 | 1/32 | 1/32 | 1/32 | >8 | >8 | >8 | >8 |

TABLE 1-continued

| Compound (II) | | Minimum rate (lb./acre) | | | | | | | |
|---|---|---|---|---|---|---|---|---|---|
| | | Control | | | | Phytotoxicity | | | |
| R³ | NR¹R² | CG | BG | YF | JG | M | CO | SB | P |
| SO₂Pr | N(Bu)(CH₂)₂OMe | 1/16 | 1/32 | ⅛ | 1/16 | 2 | >8 | >8 | >8 |
| SO₂Bu | N(Bu)(CH₂)₂OMe | 1/32 | 1/32 | ⅛ | 1/16 | 2 | >8 | >8 | >8 |
| SO₂Et | N(Bu)(CH₂)₂OEt | 1 | ½ | 1 | 1 | 4 | >8 | >8 | >8 |
| SO₂Pr | N(Bu)(CH₂)₂OEt | ¼ | ¼ | ¼ | ¼ | >8 | >8 | >8 | >8 |
| SO₂Bu | N(Bu)(CH₂)₂OEt | ⅛ | ⅛ | ⅛ | ⅛ | >8 | >8 | >8 | >8 |
| SO₂Et | N(Bu)(CH₂)₃OEt | 1/16 | ⅛ | ⅛ | 1/32 | >8 | >8 | >8 | >8 |
| SO₂Et | N(Et)(CH₂)₂OMe | ⅛ | 1/32 | 1/16 | ⅛ | 2 | 4 | >8 | >8 |
| SO₂Pr | N(allyl)(CH₂)₂OMe | ⅛ | ¼ | ¼ | ¼ | 1 | 2 | >8 | >8 |
| SO₂Bu | N(allyl)(CH₂)₂OMe | 1/32 | 1/32 | 1/16 | 1/32 | ½ | >8 | >8 | >8 |
| SO₂Et | N(allyl)(CH₂)₂OEt | ⅛ | ¼ | ¼ | ⅛ | 2 | >8 | >8 | >8 |
| SO₂Pr | N(allyl)(CH₂)₂OEt | 1/32 | ⅛ | 1/16 | ¼ | 2 | 4 | 4 | >8 |
| SO₂Bu | N(allyl)(CH₂)₂OEt | 1/16 | 1/16 | ⅛ | 1/16 | 1 | >8 | 4 | >8 |
| SO₂(CH₂)₂OEt | N(allyl)(CH₂)₂OMe | 1/32 | ⅛ | ⅛ | ⅛ | 2 | >8 | 4 | >8 |
| SO₂(CH₂)₂OEt | N(Et)(CH₂)₂OMe | ¼ | 1/16 | ¼ | ⅛ | 2 | >8 | 4 | >8 |
| SO₂(CH₂)₂OEt | N(Bu)(CH₂)₂OMe | ⅛ | 1/32 | 1/16 | 1/16 | 2 | 4 | >8 | >8 |
| SO₂(CH₂)₂OEt | NEt₂ | 1/32 | 1/32 | 1/32 | 1/16 | ¼ | 1 | 1 | >8 |
| SO₂(CH₂)₂OEt | N(allyl)(CH₂)₂OPr | ¼ | ½ | ¼ | ¼ | 2 | >8 | 4 | >8 |
| SO₂(CH₂)₂OMe | N(Et)(allyl)(Et) | ½ | ¼ | ¼ | ⅛ | 2 | >8 | >8 | >8 |

TABLE 1-continued

| Compound (II) | | Minimum rate (lb./acre) | | | | | | | |
|---|---|---|---|---|---|---|---|---|---|
| | | Control | | | | Phytotoxicity | | | |
| R³ | NR¹R² | CG | BG | YF | JG | M | CO | SB | P |
| SO₂(CH₂)₂OMe | N(allyl)(Bu) | ⅛ | 1/16 | ¼ | ⅛ | 4 | >8 | >8 | >8 |
| SO₂Et | N((CH₂)₃OEt)(Bu) | ⅛ | ⅛ | ¼ | ¼ | 2 | >8 | >8 | >8 |
| SO₂Pr | N((CH₂)₃OEt)(allyl) | ⅛ | ⅛ | ¼ | ¼ | 2 | 4 | >8 | >8 |
| SO₂Bu | N((CH₂)₃OEt)(allyl) | ⅛ | ¼ | ¼ | ⅛ | 1 | 4 | 4 | >8 |
| SO₂(CH₂)₂OMe | N(allyl)(Pr) | ½ | ⅛ | ⅛ | ⅛ | >8 | >8 | >8 | >8 |
| SO₂(CH₂)₂OMe | N(prop-2-ynyl)(Pr₂) | ⅛ | ¼ | 1/16 | ⅛ | >8 | 4 | >8 | >8 |
| SO₂(CH₂)₂OMe | NEt₂ | ¼ | ¼ | ¼ | ¼ | 2 | 2 | 4 | >8 |
| SO₂(CH₂)₂OEt | NPr₂ | 1/32 | 1/16 | 1/32 | 1/32 | 4 | 2 | >8 | >8 |
| SO₂(CH₂)₂OMe | N(allyl)₂ | 1/32 | 1/16 | 1/16 | 1/32 | 4 | 2 | 2 | 4 |
| SO₂(CH₂)₂OEt | N(allyl)₂ | 1/32 | 1/16 | 1/16 | 1/32 | ½ | 2 | >8 | >8 |
| SO₂(CH₂)₂OMe | N(Et)(prop-2-ynyl) | 1 | ⅛ | ¼ | ¼ | 4 | >8 | >8 | >8 |
| SO₂(CH₂)₂OEt | N(Et)(prop-2-ynyl) | 1/16 | ½ | ¼ | ¼ | 4 | 2 | >8 | >8 |
| SO₂(CH₂)₂OEt | N(Pr)Hex | 1 | ¼ | ¼ | ¼ | >8 | >8 | >8 | >8 |
| SO₂(CH₂)₂OMe | N(allyl)Pr | ⅛ | ¼ | ⅛ | ⅛ | 1 | 2 | 2 | >8 |
| SO₂(CH₂)₂OMe | N(Pr)(prop-2-ynyl) | ½ | 1 | ¼ | ¼ | >8 | 4 | 4 | >8 |
| SO₂(CH₂)₂OMe | N(i-Pr)Pr | ⅛ | ⅛ | ¼ | ¼ | 2 | 4 | 4 | 4 |
| SO₂(CH₂)₂OMe | N(s-Bu)Pr | ⅛ | ¼ | ¼ | 1 | >8 | >8 | >8 | >8 |
| SO₂(CH₂)₂OBu | N(allyl)₂ | ¼ | ½ | ¼ | ¼ | 4 | >8 | 4 | >8 |
| SO₂(CH₂)₂OMe | N(Pr)Et | ⅛ | ¼ | ¼ | ¼ | 4 | >8 | >8 | >8 |
| SO₂s-Bu | N(Pr)((CH₂)₂OMe) | ¼ | ¼ | ¼ | ¼ | 1 | 4 | 4 | 4 |
| SO₂(CH₂)₂OEt | N(allyl)Bu | ¼ | ½ | ¼ | ¼ | 4 | >8 | >8 | >8 |
| SO₂(CH₂)₂OEt | N(s-Bu)Et | ¼ | ¼ | ¼ | ¼ | 1 | 4 | 1 | >8 |
| SO₂(CH₂)₂OEt | N(i-Pen)Et | ½ | ¼ | ¼ | ½ | 4 | >8 | 4 | >8 |
| SO₂(CH₂)₃OMe | allyl | 1/16 | 1/16 | 1/16 | 1/16 | 1 | 2 | 4 | >8 |
| SO₂(CH)₂Oi-Pr | N(Pr)(Pr) | 1/16 | 1/16 | 1/16 | 1/16 | 2 | 2 | 2 | >8 |
| SO₂CHMeCH₂OPr | N(allyl)(Pr) | 1/16 | 1/16 | 1/16 | 1/16 | 2 | 2 | 4 | >8 |
| SO₂(CH₂)₂Oi-Pr | N(allyl)(Et) | 1/16 | 1/16 | 1/16 | 1/16 | 1 | >8 | 4 | >8 |
| SO₂(CH₂)₂OEt | N(Et)Hex(Bu) | ¼ | ¼ | ¼ | ¼ | 4 | >8 | >8 | >8 |
| SO₂CHMeCH₂OPr | N(Et)Bu | 1/16 | 1/16 | 1/16 | 1/16 | ½ | >8 | 2 | >8 |
| SO₂(CH₂)₂OMe | N(Pr)Et | ⅛ | ¼ | ¼ | ¼ | 4 | >8 | >8 | >8 |
| SO₂(CH₂)₂OEt | N(Pr)Et | ¼ | ¼ | ¼ | ¼ | 4 | >8 | >8 | >8 |
| SO₂(CH₂)₃OMe | N(Bu)Et | 1/16 | 1/16 | 1/16 | ⅛ | ½ | >8 | >8 | >8 |

TABLE 1-continued

| Compound (II) | | Minimum rate (lb./acre) | | | | | | | |
|---|---|---|---|---|---|---|---|---|---|
| | | Control | | | | Phytotoxicity | | | |
| R³ | NR¹R² | CG | BG | YF | JG | M | CO | SB | P |
| SO₂(CH₂)₂OMe | N(Bu)Et | ⅛ | ¼ | 1/16 | 1/16 | >8 | 2 | 4 | >8 |
| SO₂(CH₂)₂OEt | N(allyl)Hex | 1 | ½ | ¼ | ¼ | >8 | >8 | >8 | >8 |
| SO₂Et | N((CH₂)₂OPr)(Et) | ¼ | ½ | ¼ | ¼ | 2 | >8 | >8 | >8 |
| SO₂Pr | N((CH₂)₂OPr)(Et) | ¼ | ½ | ¼ | ¼ | >8 | >8 | >8 | >8 |
| SO₂s-Bu | N(Et)(Et) | ¼ | ¼ | ¼ | ¼ | 1 | 4 | 4 | 4 |
| SO₂Pent | N((CH₂)₂OEt)(Pr) | ¼ | ¼ | ¼ | ¼ | 2 | 4 | 4 | >8 |
| SO₂s-Bu | N((CH₂)₂OMe)(Pr) | ½ | ¼ | ½ | ¼ | 2 | >8 | 4 | >8 |
| SO₂Pr | N((CH₂)₂OEt)(Pr) | ½ | ¼ | ¼ | ¼ | >8 | >8 | >8 | >8 |
| SO₂Bu | N(CH₂OMe)(Pr) | ½ | ¼ | ¼ | ¼ | >8 | >8 | >8 | >8 |
| SO₂(CH₂)₂OEt | N(CH₂OMe)(Pr) | ¼ | ¼ | ¼ | ¼ | 4 | >8 | >8 | >8 |
| SO₂Pr | N((CH₂)₂OMe)(Et) | ¼ | ¼ | ¼ | ¼ | 2 | 2 | 2 | 2 |
| SO₂i-Pr | N((CH₂)₃OEt)(Et) | ¼ | ¼ | ¼ | ¼ | 1 | 2 | 2 | >8 |
| SO₂Bu | N((CH₂)₃OEt)(Et) | ¼ | ¼ | ¼ | ¼ | 1 | 4 | 2 | >8 |
| SO₂i-Bu | N((CH₂)₃OEt)(Et) | ¼ | ¼ | ¼ | ¼ | 2 | 2 | 2 | >8 |
| SO₂Pen | N((CH₂)₃OEt)(Et) | ½ | ½ | ¼ | ½ | >8 | >8 | >8 | >8 |
| SO₂(CH₂)₂OMe | N((CH₂)₃OEt)(i-Bu) | ½ | 1 | ½ | ⅛ | 4 | 4 | 4 | 4 |
| SO₂(CH₂)₂OEt | N(allyl)(i-Bu) | 1/16 | 1 | ¼ | ¼ | >8 | >8 | >8 | >8 |
| SO₂(CH₂)₂OMe | N(allyl)(Pen) | 1/16 | ⅛ | ¼ | ⅛ | 4 | >8 | >8 | >8 |

TABLE 1-continued

| Compound (II) | | Minimum rate (lb./acre) Control | | | | Phytotoxicity | | | |
|---|---|---|---|---|---|---|---|---|---|
| R³ | NR¹R² | CG | BG | YF | JG | M | CO | SB | P |
| $SO_2(CH_2)_2OEt$ | N(Pen)(allyl) | 1/16 | ⅛ | 1/16 | 1/16 | 2 | >8 | >8 | >8 |
| $SO_2Et$ | N(Et)((CH$_2$)$_3$OMe) | 1/16 | 1/16 | ⅛ | ⅛ | 1 | 2 | 4 | >8 |
| $SO_2Pr$ | N(Et)((CH$_2$)$_3$OMe) | 1/16 | 1/16 | 1/16 | 1/16 | 1 | 2 | 2 | >8 |
| $SO_2Pr$ | N(Et)(CHMeCH$_2$OPr) | ¼ | 1 | ¼ | ¼ | 4 | >8 | >8 | >8 |
| $SO_2Bu$ | N(Et)(CHMeCH$_2$OPr) | ¼ | ½ | ¼ | ¼ | >8 | >8 | >8 | >8 |
| $SO_2Bu$ | N(Et)((CH$_2$)$_3$OMe) | 1/16 | ¼ | 1/16 | 1/16 | 2 | 4 | >8 | >8 |
| $SO_2(CH_2)_2OEt$ | N(2-methylallyl)$_2$ | ¼ | ¼ | ½ | ¼ | >8 | >8 | >8 | >8 |
| $SO_2(CH_2)_2OMe$ | N(2-methylallyl)$_2$ | ¼ | ¼ | ¼ | ¼ | 1 | 4 | 2 | >8 |
| $SO_2Pr$ | N(Et)((CH$_2$)$_2$O—i-Pr) | 1/16 | ¼ | ⅛ | ¼ | 1 | >8 | >8 | >8 |
| $SO_2(CH_2)_2OEt$ | N(Et)((CH$_2$)$_2$O—i-Pr) | ¼ | ¼ | ¼ | ¼ | 1 | >8 | >8 | >8 |
| $SO_2(CH_2)_2OMe$ | N(Pr)((CH$_2$)$_2$OMe) | ¼ | ½ | ¼ | ½ | >8 | >8 | >8 | >8 |
| $SO_2(CH_2)_2OMe$ | N(Et)((CH$_2$)$_2$OEt) | 1/32 | 1/16 | 1/32 | 1/32 | ½ | >8 | >8 | >8 |
| $SO_2Et$ | N(Et)(2-chloro-ethyl) | ¼ | ¼ | ¼ | 1 | >8 | >8 | >8 | >8 |
| $SO_2Et$ | N(Pr)(2-chloro-ethyl) | 1/16 | ⅛ | ⅛ | 1/16 | ½ | 2 | 2 | 1 |
| $SO_2Et$ | N(Pr)(2-chloro-ethyl) | ¼ | ¼ | ¼ | 1 | >8 | >8 | >8 | >8 |
| $SO_2Pr$ | N(Pr)(2-chloro-allyl) | 1/16 | 1/16 | ¼ | ⅛ | 4 | >8 | >8 | >8 |
| $SO_2$i-Pr | N(Pr)(2-chloro-allyl) | ⅛ | 1/16 | ¼ | ¼ | >8 | >8 | >8 | >8 |
| $SO_2$i-Bu | N(Pr)(2-chloro-allyl) | ¼ | ¼ | ¼ | ¼ | >8 | >8 | >8 | >8 |
| SOCHClPr | NPr$_2$ | ¼ | ¼ | ¼ | ¼ | >8 | >8 | >8 | >8 |

TABLE 1-continued

| Compound (II) | | Minimum rate (lb./acre) | | | | | | | |
| --- | --- | --- | --- | --- | --- | --- | --- | --- | --- |
| | | Control | | | | Phytotoxicity | | | |
| R³ | NR¹R² | CG | BG | YF | JG | M | CO | SB | P |
| SO₂s-Bu | Pr / N \ 2-chloro-allyl | 1 | ⅛ | ¼ | ¼ | >8 | >8 | 4 | >8 |
| SO₂(CH₂)₂OEt | Et / N \ 2-chloro-allyl | ½ | ¼ | ½ | ¼ | >8 | >8 | >8 | >8 |
| SO₂Me | Pr / N \ 2-chloro-ethyl | 1/16 | ¼ | ¼ | ¼ | 4 | 4 | 2 | 4 |
| SO₂Bu | Pr / N \ 2-chloro-allyl | ¼ | ½ | ½ | ¼ | >8 | >8 | >8 | >8 |
| SO₂Pen | Pr / N \ 2-chloro-allyl | ¼ | ½ | ¼ | ½ | >8 | >8 | >8 | >8 |
| SO₂(CH₂)₂OMe | Pr / N \ 2-chloro-allyl | ½ | ½ | ¼ | ¼ | >8 | >8 | >8 | >8 |
| SO₂Et | Et / N \ 2-chloro-allyl | ⅛ | ⅛ | ¼ | ¼ | >8 | >8 | >8 | >8 |
| SO₂Pr | Et / N \ 2-chloro-allyl | ⅛ | ¼ | ¼ | ¼ | >8 | >8 | >8 | >8 |
| SO₂(CH₂)₂OEt | allyl / N \ 2-chloro-allyl | ½ | 1 | ½ | ½ | >8 | >8 | >8 | >8 |
| SO₂(CH₂)₂OMe | Et / N \ 2-chloro-allyl | ¼ | ⅛ | ¼ | ½ | 4 | 4 | >8 | >8 |
| SO₂(CH₂)₂OEt | Et / N \ 2-chloro-allyl | ¼ | ¼ | ⅛ | ⅛ | 2 | 4 | >8 | >8 |
| SO₂(CH₂)₂OEt | N(cyclopropyl)Et | ½ | ½ | ½ | ¼ | 2 | 2 | 2 | >8 |
| SO₂Et | N(cyclopropyl)Et | 1/32 | 1/32 | 1/32 | 1/32 | ½ | 4 | >8 | 4 |
| SO₂Pr | N(cyclopropyl)Et | 1/32 | 1/32 | 1/16 | ⅛ | ½ | 4 | >8 | 4 |
| SO₂i-Pr | N(cyclopropyl)Et | 1/32 | 1/32 | ¼ | 1/16 | 1 | 2 | 2 | >8 |
| SO₂Bu | Et / N \ cyclopropyl | 1/32 | 1/32 | ⅛ | ⅛ | ½ | 4 | 2 | 4 |
| SO₂Et | Pr / N \ cyclopropyl | 1/16 | 1/16 | ½ | ½ | 2 | >8 | >8 | >8 |
| SO₂Pr | Pr / N \ cyclopropyl | 1/16 | ⅛ | ¼ | ¼ | 2 | >8 | >8 | >8 |
| SO₂i-Pr | Pr / N \ cyclopropyl | ⅛ | ⅛ | 1/16 | ¼ | 2 | >8 | >8 | >8 |
| SO₂Bu | Pr / N \ cyclopropyl | 1/16 | 1/16 | ⅛ | ⅛ | 1 | >8 | >8 | >8 |

For purposes of comparison, various 1,2,4-triazoles within the scope of the isomeric formulae A but outside the scope of the formulae, I, II and III (compounds of the formula III are wholly outside the scope of formulae A), were included in the glasshouse trials described above, using application rates logarithmically reducing from 32 lb./acre. The results obtained are given in the following Tables 2 and 3, in which "*" designates a compound that is specifically exemplified in U.S. Pat. No. 3,308,131. The compounds that give no control of any of the words crabgrass, barnyard grass, yellow foxtail and Johnson grass at the maximum application rate of 32 lb./acre are listed in Table 3. In view of their lack of activity against the weeds, these compounds were not included in the crop tests. Of the compounds listed in Table 3, those that are believed to have been obtained as a mixture of isomers (corresponding to formulae A) containing appreciably more than 10% of each isomer, or those in which the isomeric structure is uncertain, are designated 1(2)- in the nomenclature of the carbamoyl group. The remaining compounds are believed to have been obtained substantially as the isomer given, or predominantly as this isomer with less than 10% of the other isomer.

TABLE 2

| Compound (I, X = O, R$^8$ = H) | | Minimum rate (lb./acre) | | | | | | | |
|---|---|---|---|---|---|---|---|---|---|
| | | control | | | | phytotoxicity | | | |
| R$^7$ | NR$^5$R$^6$ | CG | BG | YF | JG | CO | SB | M | F |
| *Mo | NMe$_2$ | 1 | 16 | 2 | 2 | 4 | 8 | 4 | 8 |
| *Cl | " | 4 | 2 | 2 | 2 | 2 | 4 | 2 | 4 |
| *Br | " | 4 | 4 | 32 | 4 | 1 | 1 | 2 | 4 |
| *SMe | " | 1 | 4 | 4 | 2 | ½ | 2 | 2 | 2 |

TABLE 3

Compounds with the following substituents on the 1,2,4-triazole ring gave no weed control at 32 lb./acre.

*1-dimethylcarbamoyl
*1-dimethylthiocarbamoyl
1(2)-dimethylthiocarbamoyl-3-ethylthio
1(2)-diethylthiocarbamoyl-3-ethylthio
*1(2)-dimethylthiocarbamoyl-3-methylthio-5-methyl
*1(2)-dimethylcarbamoyl-3-methylsulphonyl-5-methyl
*1(2)-diethylcarbamoyl-3-methylthio-5-methyl
*1(2)-N-methyl-N-n-butylcarbamoyl-3-methylthic-5-methyl
*1(2)-dimethylcarbamoyl-3-ethylthio-5-methyl
*1-dimethylcarbamoyl-3-dodecylthio-5-methyl
1-dimethylcarbamoyl-3-n-hexylthio
1-dimethylcarbamoyl-3-cyclohexylthio
1-dimethylcarbamoyl-3-dodecylthio
*1-dimethylcarbamoyl-3-undecyl-5-methylthio
1-dimethylcarbamoyl-3-benzyl
*1-dimethylcarbamoyl-3-benzylthio-5-methyl
*1-dimethylcarbamoyl-3-phenyl-5-methylthio
*1-dimethylcarbamoyl-3-p-nitrophenylthio-5-methyl
1-dimethylcarbamoyl-3-(2,4-dinitrophenylthio)
*1-dimethylcarbamoyl-3,5-dimethyl
*1-dimethylcarbamoyl-3-(2-diethylaminoethylthio)-5-methyl
*1-dimethylcarbamoyl-3-ethoxycarbonylmethylthio-5-methyl
*1-dimethylcarbamoyl-3-(1-dimethylcarbamoyl-1,2,4-triazol-3-yldithio)
*1-(4-methylpiperidinocarbonyl)
*1(2)-pyrrolidinocarbonyl-3-methylthio-5-methyl
1-piperidinocarbonyl-3-ethylthio
1(2)-(4-methylpiperazinocarbonyl)-3-ethylthio
1-(1,2,3,4-tetrahydroquinolincarbonyl)-3-ethylthio
1(2)-(N-methyl-N-methoxycarbamoyl)-3-ethylthio
1-diallylcarbamoyl
1(2)-diallylcarbamoyl-3-ethylthio-5-methyl
1-diallylcarbamoyl-3-(2-diethylaminoethylthio)
1-diallylcarbamoyl-3-methoxycarbonylmethyl TABLE 3-continued Compounds with the following substituents on the 1,2,4-triazole ring gave no weed control at 32 lb./acre.

1-di(cyanomethyl)carbamoyl-3-ethylthio

The results given above show that the compounds listed in Tables 1, are markedly superior to the compounds listed in Tables 2 and 3 in respect of their high level of selective pre-emergence activity against all four of the weeds crabgrass, barnyard grass, yellow foxtail and Johnson grass in the crops cotton, soyabean, maize and peanut.

It can be seen from the foregoing description that the compounds of the present invention are of value for the pre-weed emergence control of graminaceous weeds in a variety of crops, for example cotton, leguminous crops such as soyabean and peanut, and cereals such as maize. However, it will be appreciated that the individual compounds of the present invention are not all equivalent in their level of herbicidal activity and selectivity characteristics. Accordingly the optimum compound for one particular use is not necessarily the optimum compound for another particular use.

Insecticidal and miticidal tests have been carried out with a variety of compounds of the present invention. The compounds tested were found to have little or no activity against insects, for example *Plutella maculipennis, Phaedon cochlearieae,* and aphids such as *Aphis fabae* and *Megoura viciae.* The compounds tested were also found to have little or no activity against mites, for example *Tetrasychus urticae.*

Regarding the mammalian toxicity of the compounds of the present invention, acute oral toxicity studies in mice have given satisfactory results. In these studies, the compounds of the present invention have been found to be less toxic than certain closely related 1,2,4-triazoles, for example 1-dimethylcarbamoyl-3-methylthio-1,2,4-triazole.

PREPARATION OF COMPOUNDS OF FORMULA II

The compounds of formula II may be prepared by the hereinafter described processes, which are analogous to known processes for preparing similar compounds.

One such process comprises reacting a triazole of the general formula

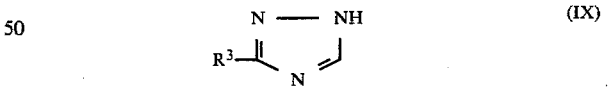

(IX)

in which R$^3$ is as hereinbefore defined for formula II, with a carbamoyl halide of the general formula Z-COHR$^1$R$^2$ (X) in which R$^1$ and R$^2$ are as hereinbefore defined for formula II and Z is chlorine, fluorine or bromine, preferably chlorine. The reaction is suitably effected in the presence of an inert organic liquid as the reaction medium, which is preferably a solvent for the reactions. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula IX may be converted to an alkali metal (for example sodium) salt thereof prior to the reaction with the carbamoyl halide. The alkali metal salt may be obtained by reacting the triazole of the general formula IX with an alkali metal hydride, amide or alkoxide, in accordance with known methods.

The carbamoyl halides of the general formula X may be prepared by reacting a secondary amine of the general formula HNR¹R², in which R¹ and R² are as defined above, with a carbonyl halide COZ₂, in accordance with known methods.

The compounds of formula II may also be prepared by a process which comprises reacting a carbamoyl halide of the general formula

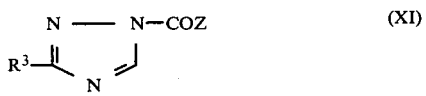  (XI)

in which R³ and Z are as defined above, with a secondary amine of the general formula HNR¹R², in which R¹ and R² are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula XI may be prepared from the triazoles of general formula IX by reaction with a carbonyl COZ₂, preferably phosgene, in accordance with known methods.

The triazoles of general formula IX may be prepared by alkylation or alkenylation of 3-mercapto-1,2,4-triazole (e.g. by reaction of 3-mercapto-1,2,4-triazole with a compound R³-Y wherein Y is chloro or bromo), followed by oxidation of the 3-thio group where appropriate, in accordance with known methods.

The compounds of formula II may also be prepared by a process which comprises reacting a carbonylbis-triazole of the general formula

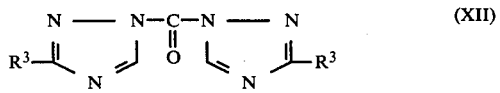  (XII)

in which R³ is as defined above, with a secondary amine of the general formula HNR¹R², in which R¹ and R² are as defined above. The reaction is suitably effected in the presence of an inert organic liquid as the reaction medium, which is preferably a solvent for the reactants.

The carbonylbistriazoles of the general formula XII may be prepared by reacting a triazole of the hereinbefore defined general formula IX with about 0.5 molecular proportions of a carbonyl halide COZ₂, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula HNR¹R².

It will be appreciated by those skilled in the art that the triazoles represented by the general formula IX are tautomeric and that, for convenience, general formula IX depicts the structure of one tautomer.

The compounds of formula II in which R³ is an alkoxyalkylsulphinyl, haloalkylsulphinyl, alkylsulphonyl, alkoxyalkylsulphonyl, or haloalkylsulphonyl group may also be prepared by a process which comprises the oxidation of a compound of the general formula

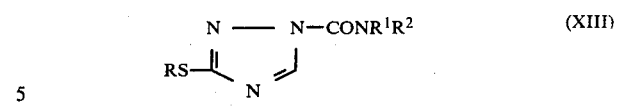  (XIII)

in which R is an appropriate alkyl, alkoxyalkyl or haloalkyl group and R¹ and R² are as defined above, in accordance with known methods. The oxidation may be effected, for example, by reaction with hydrogen peroxide or peracetic acid.

The intermediate triazoles of the general formula IX, with the exception of the compounds in which R³ is methylsulphonyl are novel compounds.

It will be appreciated by those skilled in the art that the acylation reactions described above in the preparations of compounds of formulae I, II and III can theoretically give two isomeric products, one (hereinafter referred to as 1-isomer) having the general formula I, II or III and the other (hereinafter referred to as 2-isomer) having the general formula

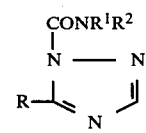

where R is the group R³ of formulae I or II or the group R³R⁴NO₂S- of formula III.

It is believed that the solid compounds of the present invention, after purification by standard methods such as crystallization, are obtained as substantially pure 1-isomer. The liquid compounds of the present invention, as isolated by standard methods such as distillation in vacuo, are believed to be obtained as components of an isomeric mixture consisting predominantly of the 1-isomer together with a minor proportion, generally less than about 10% of 2-isomer.

The following Examples illustrate the invention.

EXAMPLE 1

This Example illustrates the preparation of compounds of formula II.

A solution of 4.1 g. 3-(2-ethoxyethylsulphonyl)-1,2,4-triazole, 3.5 g. diallylcarbamoyl chloride and 4 ml. triethylamine in 40 ml. dry tetrahydrofuran was refluxed under anhydrous conditions for 15 hours. The cooled reaction mixture was filtered to remove triethylamine hydrochloride and the filtrate was evaporated to remove solvent. The residue was triturated with petroleum ether (b.p. 40°–60° C.) to give a solid product. This product was collected and recrystallised from ether/petroleum ether b.p. 40°–60° C. to give 1-diallylcarbamoyl-3-(2-ethoxyethylsulphonyl)-1,2,4-triazole, m.p. 62°–63° C. Elemental analysis satisfactory.

The novel intermediate triazole compounds used in the above preparation were prepared as follows. To a solution of 11.8 g. sodium in 350 ml. absolute ethanol was added 52.5 g. 1,2,4-triazole-3-thiol. To the resulting solution was added 84 g. 1-bromo-2-ethoxyethane and the resulting solution refluxed for 3 hours. The cooled reaction mixture was filtered, the filtrate was evaporated under reduced pressure to remove solvent, and the residue was dissolved in ether. The resulting solution was filtered, the filtrate was evaporated to remove solvent and the residue distilled under reduced pressure to give 3-(2-ethoxyethylthio)-1,2,4-triazole, b.p. 337°–345° C./0.3–0.5 mm. Elemental analysis satisfactory.

Hydrogen peroxide (33.6 ml. of 100 vol. solution) was added in small portions to a solution of 17.3 g. 3-(2-ethoxyethylthio)-1,2,4-triazole in 150 ml. glacial acetic acid, maintaining the temperature of the reaction mixture at 80°–85° C. When the addition of hydrogen peroxide was complete, the temperature of the reaction mixture was maintained at 80°–85° C. for an additional period of 2 hours. The reaction mixture was distilled under reduced pressure to remove acetic acid and the solid residue obtained was crystallized from ethyl acetate/petroleum ether, b.p. 40°–60° C. to give 3-(2-ethoxyethylsulphonyl)-1,2,4-triazole, m.p. 91.5°–92.5° C.

In an analogous manner to that described above, the following compounds were prepared:

1-dipropylcarbamoyl-3-(2-methoxyethylsulphonyl)-1,2,4-triazole, m.p. 76°–77° C.
1-dipropylcarbamoyl-3-(2-ethoxyethylsulphonyl)-1,2,4-triazole, m.p. 51°–52° C.
1-diallylcarbamoyl-3-(2-methoxyethylsulphonyl)-1,2,4-triazole, m.p. 47°–47.5° C.
1-diallylcarbamoyl-3-(2-methoxyethylsulphinyl)-1,2,4-triazole, an oil, $n_D^{25}$ 1.5058

Novel intermediates 3-(2-methoxyethylthio)-1,2,4-triazole, m.p. 53°–54° C.
3-(2-methoxyethylsulphonyl)-1,2,4-triazole, m.p. 80°–82° C.

Satisfactory elemental analyses were obtained for all the above-mentioned products.

EXAMPLE 2

This Example illustrates the preparation of compounds of formula II.

A solution of 5.67 g. 3-isobutylsulphonyl-1,2,4-triazole, 5.16 g. N-ethyl-N-(2-methoxyethyl)carbamoyl chloride, 6 ml. triethylamine and 40 ml. dry tetrahydrofuran was kept at ambient temperature (20° C.) for 72 hours. The mixture was filtered to remove triethylamine hydrochloride and the filtrate was evaporated to give a residual oil. This oil was washed with petroleum ether, b.p. 40°–60° C. (3×100 ml.) and then dissolved in ether. The ethereal solution was filtered to remove a trace of insoluble material and the filtrate was evaporated to give a residual oil which was kept at 100° C. in vacuo for 2 hours to remove all traces of volatile material. There was thus obtained 1-[N-ethyl-N-(2-methoxyethyl)carbamoyl]-3-isobutylsulphonyl-1,2,4-triazole as an oil, $n_D^{25}$ 1.4984.

In an analogous manner to that described above, the following compounds were prepared.

1-[N-propyl-N-(2-ethoxyethyl)carbamoyl]-3-propylsulphonyl-1,2,4-triazole, an oil, $n_D^{25}$ 1.4918
1-[N-propyl-N-(2-ethoxyethyl)carbamoyl]-3-isopropylsulphonyl-1,2,4-triazole, an oil, $n_D^{23}$ 1.4940
1-[N-propyl-N-(2-ethoxyethyl)carbamoyl]-3-n-butylsulphonyl-1,2,4-triazole, an oil, $n_D^{23}$ 1.4906
1-[N-propyl-N-(2-ethoxyethyl)carbamoyl]-3-isobutylsulphonyl-1,2,4-triazole, an oil, $n_D^{23}$ 1.4906
1-[N-ethyl-N-(2-methoxyethyl)carbamoyl]-3-propylsulphonyl-1,2,4-triazole, an oil, $n_D^{25}$ 1.5008
1-[N-ethyl-N-(2-methoxyethyl)carbamoyl]-3-isopropylsulphonyl-1,2,4-triazole, an oil, $n_D^{24}$ 1.5020
1-[N-ethyl-N-(2-methoxyethyl)carbamoyl]-3-n-butylsulphonyl-1,2,4-triazole, an oil, $n_D^{24}$ 1.4954
1-[N-propyl-N-(2-methoxyethyl)carbamoyl]-3-propylsulphonyl-1,2,4-triazole, m.p. 45°–45.5° C.
1-[N-propyl-N-(2-methoxyethyl)carbamoyl]-3-isopropylsulphonyl-1,2,4-triazole, an oil, $n_D^{24}$ 1.4978
1-[N-propyl-N-(2-methoxyethyl)carbamoyl]-3-n-butylsulphonyl-1,2,4-triazole, an oil, $n_D^{24}$ 1.4960
1-[N-propyl-N-(2-methoxyethyl)carbamoyl]-3-isobutylsulphonyl-1,2,4-triazole, an oil, $n_D^{25}$ 1.4942
1-[N-ethyl-N-(2-ethoxyethyl)carbamoyl]-3-ethylsulphonyl-1,2,4-triazole, an oil, $n_D^{25}$ 1.5000
1-[N-ethyl-N-(2-ethoxyethyl)carbamoyl]-3-propylsulphonyl-1,2,4-triazole, an oil, $n_D^{25}$ 1.4960
1-[N-ethyl-N-(2-ethoxyethyl)carbamoyl]-3-isopropylsulphonyl-1,2,4-triazole, an oil, $n_D^{25}$ 1.4952
1-[N-ethyl-N-(2-ethoxyethyl)carbamoyl]-3-n-butylsulphonyl-1,2,4-triazole, an oil, $n_D^{25}$ 1.4918
1-[N-propyl-N-(2-methoxyethyl)carbamoyl]-3-ethylsulphonyl-1,2,4-triazole, an oil, $n_D^{24}$ 1.5005
1-[N-ethyl-N-(2-methoxyethyl)carbamoyl]-3-ethylsulphonyl-1,2,4-triazole, an oil, $n_D^{24}$ 1.5036
1-[N-ethyl-N-(3-ethoxypropyl)carbamoyl]-3-ethylsulphonyl-1,2,4-triazole, an oil, $n_D^{25}$ 1.4975
1-[N-propyl-N-(2-ethoxyethyl)carbamoyl]-3-ethylsulphonyl-1,2,4-triazole, an oil, $n_D^{24}$ 1.4956

Novel intermediate compounds used in the preparation described above were prepared as follows. N-ethyl-N-2-methoxyethylamine, b.p. 115°–116° C., was prepared by reaction of 3 molecular proportions of ethylamine with 1 molecular proportion of 1-bromo-2-methoxyethane in aqueous solution containing 1 equivalant of sodium hydroxide at 30°–50° C. To a stirred solution of 89.1 g. phosgene in 500 ml. dry ether at −20° C. was added a solution of 30.9 g. N-ethyl-N-2-methoxyethylamine in 50 ml. dry ether, maintaining the temperature of the reaction mixture at −20° C. The stirred mixture was then allowed to warm to room temperature during 1 hour. The reaction mixture was filtered and the filtrate evaporated in vacuo below 25° C. to remove the solvent and give the product, N-(2-methoxyethyl)-N-ethylcarbamoyl chloride as a pale yellow liquid.

The following novel intermediates were prepared in an analogous manner.

N-propyl-N-2-methoxyethylamine, b.p. 138° C.
N-propyl-N-(2-methoxyethyl)carbamoyl chloride
N-propyl-N-2-ethoxyethylamine, b.p. 154°–155° C.
N-propyl-N-(2-ethoxyethyl)carbamoyl chloride
N-ethyl-N-2-methoxyethylamine, b.p. 116° C.
N-ethyl-N-(2-methoxyethyl)carbamoyl chloride
N-ethyl-N-3-ethoxypropylamine, b.p. 155°–156° C.
N-ethyl-N-(3-ethoxypropyl)carbamoyl chloride The following novel intermediates were prepared by a method analogous to that described in Example 52.

3-propylsulphonyl-1,2,4-triazole, m.p. 116°–117° C.
3-isopropylsulphonyl-1,2,4-triazole, m.p. 170°–171° C.
3-n-butylsulphonyl-1,2,4-triazole, m.p. 96°–97° C.
3-isobutylsulphonyl-1,2,4-triazole, m.p. 157°–158.5° C.
3-ethylsulphonyl-1,2,4-triazole, m.p. 145° C.

EXAMPLE 2

This Example illustrates the preparation of compounds of formula II.

A solution of 0.03 mole of 3-(2-methoxyethylsulphonyl)-1,2,4-triazole, 6 ml. of triethylamine and 0.033 mole of N-ethyl-N-isopropylcarbamoyl chloride in 40 ml. of dry tetrahydrofuran was heated under reflux for 15 hours. The cooled reaction mixture was filtered to remove triethylamine hydrochloride and the filtrate was evaporated to remove solvent. The product crystallized on cooling and treatment with 100 ml. of petroleum ether (b.p. 62°–68° C.). Thin solid was collected and recrystallized from 100 ml. benzene petroleum ether (b.p. 40°–60° C.) to give 1-(N-ethyl-N-isopropylcarbamoyl)-3-(2-methoxyethylsulphonyl)-1,2,4-triazole, m.p. 64°–65° C. Elemental analysis satisfactory.

The intermediate, 3-(2-methoxyethylsulphonyl)-1,2,4-triazole, was prepared by a method analogous to that described in Example 52.

The carbamoyl chloride intermediate was prepared in the following way. Phosgene was passed into 100 ml. of refluxing ethyl acetate until the liquid was saturated with phosgene. To the refluxing, stirred solution was added dropwise a solution of N-ethyl-isopropylamine in 100 ml. ethyl acetate. When the addition was complete the flow of phosgene into the stirred, refluxing reaction mixture was maintained for 30 minutes. The reaction mixture was distilled under reduced pressure to remove the solvent and give the product N-ethyl-N-isopropylcarbamoyl chloride.

In an analogous manner to that described above the following compounds were prepared:

1-dipropylcarbamoyl-3-(2-ethoxyethylsulphonyl)-1,2,4-triazole, m.p. 51°–52° C.

1-diallylcarbamoyl-3-(2-ethoxyethylsulphonyl)-1,2,4-triazole, m.p. 62°–63° C.

1-(N-butyl-N-ethylcarbamoyl)-3-(2-ethoxyethylsulphonyl)-1,2,4-triazole, b.p. 185°–188° C./0.2 mm.

1-(N-allyl-N-propylcarbamoyl)-3-(2-ethoxyethylsulphonyl)-1,2,4-triazole, m.p. 51°–52° C.

1-(N-propyl-N-2-propynylcarbamoyl)-3-(2-ethoxyethylsulphonyl)-1,2,4-triazole, m.p. 68°–70° C.

1-(N-allyl-N-ethylcarbamoyl)-3-(2-methoxyethylsulphonyl)-1,2,4-triazole, m.p. 58.5°–59.5° C.

1-(diethylcarbamoyl)-3-(2-methoxyethylsulphonyl)-1,2,4-triazole, m.p. 46°–47° C.

1-(N-allyl-N-butylcarbamoyl)-3-(2-ethoxyethylsulphonyl)-1,2,4-triazole, b.p. 192°–194° C./0.35 mm.

1-(N-allyl-N-butylcarbamoyl)-3-(2-methoxyethylsulphonyl)-1,2,4-triazole, m.p. 48°–50° C.

1-(N-allyl-N-propylcarbamoyl)-3-(2-methoxyethylsulphonyl)-1,2,4-triazole, m.p. 60°–61° C.

1-(diethylcarbamoyl)-3-(2-propoxyethylsulphonyl)-1,2,4-triazole, m.p. 57.5°–58° C.

1-(diethylcarbamoyl)-3-(3-ethoxypropylsulphonyl)-1,2,4-triazole, an oil, $n_D^{21}$ 1.5012 (95.8% 1-isomer by GLC assay)

1-(N-ethyl-N-2-propynylcarbamoyl)-3-(2-methoxyethylsulphonyl)-1,2,4-triazole, m.p. 56°–58° C.

1-(N-propyl-N-hexylcarbamoyl)-3-(2-ethoxyethylsulphonyl)-1,2,4-triazole, an oil, $n_D^{21}$ 1.4931 (98.4% 1-isomer by GLC assay)

1-(N-ethyl-N-isopropylcarbamoyl)-3-(2-methoxyethylsulphonyl)-1,2,4-triazole, m.p. 85°–85.5° C.

1-(N-ethyl-N-isopropylcarbamoyl)-3-(2-ethoxyethylsulphonyl)-1,2,4-triazole, m.p. 64°–65° C.

1-(N-propyl-N-2-propynylcarbamoyl)-3-(2-methoxyethylsulphonyl)-1,2,4-triazole, m.p. 61°–63° C.

1-(N-propyl-N-isopropylcarbamoyl)-3-(2-methoxyethylsulphonyl)-1,2,4-triazole, m.p. 73.5°–74.5° C.

1-(diallylcarbamoyl)-3-(3-ethoxypropylsulphonyl)-1,2,4-triazole, an oil, $n_D^{21}$ 1.5128 (97.2% 1-isomer by GLC assay)

1-(diallylcarbamoyl)-3-(2-propoxyethylsulphonyl)-1,2,4-triazole, m.p. 49°–49.5° C.

1-(N-allyl-N-propylcarbamoyl)-3-(2-methoxyethylsulphonyl)-1,2,4-triazole, m.p. 55°–55.5° C.

1-(N-propyl-N-sec.butylcarbamoyl)-3-(2-methoxyethylsulphonyl)-1,2,4-triazole, m.p. 42°–44° C.

1-(N-ethyl-N-2-propynylcarbamoyl)-3-(2-ethoxyethylsulphonyl)-1,2,4-triazole, m.p. 81.5°–83.5° C.

1-(N-propyl-N-sec.butylcarbamoyl)-3-(2-ethoxyethylsulphonyl)-1,2,4-triazole, m.p. 38°–40.5° C.

1-(N-propyl-N-isopropylcarbamoyl)-3-(2-ethoxyethylsulphonyl)-1,2,4-triazole, m.p. 73.5°–75.5° C.

1-(diallylcarbamoyl)-3-(2-butoxyethylsulphonyl)-1,2,4-triazole, an oil, $n_D^{26}$ 1.5082

1-(N-allyl-N-hexylcarbamoyl)-3-(2-methoxyethylsulphonyl)-1,2,4-triazole, an oil, $n_D^{22}$ 1.5031 (99% 1-isomer by GLC assay)

1-(N-allyl-N-hexylcarbamoyl)-3-(2-ethoxyethylsulphonyl)-1,2,4-triazole, an oil, $n_D^{22}$ 1.5016 (97.5% 1-isomer by GLC assay)

1-(N-propyl-N-sec.butylcarbamoyl)-3-(2-ethoxyethylsulphonyl)-1,2,4-triazole, m.p. 38°–40.5° C.

1-(N-ethyl-N-butylcarbamoyl)-3-(2-methoxyethylsulphonyl)-1,2,4-triazole, an oil, $n_D^{26}$ 1.5006

1-(N-ethyl-N-hexylcarbamoyl)-3-(2-ethoxyethylsulphonyl)-1,2,4-triazole, m.p. 42°–43° C.

1-(N-ethyl-N-hexylcarbamoyl)-3-(2-methoxyethylsulphonyl)-1,2,4-triazole, an oil, $n_D^{22}$ 1.4977 (96.3% 1-isomer by GLC assay)

1-(N-allyl-N-isobutylcarbamoyl)-3-(2-methoxyethylsulphonyl)-1,2,4-triazole, an oil, $n_D^{26}$ 1.5052

1-(N-allyl-N-isopropylcarbamoyl)-3-(2-methoxyethylsulphonyl)-1,2,4-triazole, m.p. 77°–80° C.

1-(N-allyl-N-isopropylcarbamoyl)-3-(2-ethoxyethylsulphonyl)-1,2,4-triazole, m.p. 52°–54° C.

1-(N-ethyl-N-pentylcarbamoyl)-3-(2-ethoxyethylsulphonyl)-1,2,4-triazole, m.p. 25° C.

1-(N-ethyl-N-pentylcarbamoyl)-3-(2-methoxyethylsulphonyl)-1,2,4-triazole, m.p. 25° C.

The following novel carbamoyl chloride/and triazole intermediates were prepared:

3-(3-ethoxypropylsulphonyl)-1,2,4-triazole, m.p. 115°–115.5° C.

3-(2-butoxyethylsulphonyl)-1,2,4-triazole, m.p. 101°–102° C.

N-allyl-N-propylcarbamoyl chloride, b.p. 102°–103° C./16–17 mm.

N-propyl-N-(2-propynyl)carbamoyl chloride, b.p. 56°–60° C./0.25 mm.

N-allyl-N-ethylcarbamoyl chloride, b.p. 36° C./0.05 mm.

N-allyl-N-butylcarbamoyl chloride, b.p. 76° C./0.1 mm.

N-ethyl-N-(2-propynyl)carbamoyl chloride

N-propyl-N-(2-propynyl)carbamoyl chloride

EXAMPLE 4

This Example illustrates the preparation of compounds of formula II.

A solution of 0.03 mole of 3-propylsulphonyl-1,2,4-triazole, 11 ml. of triethylamine, 6.85 g. of N-butyl-N-(2-ethoxyethyl)carbamoyl chloride in 40 ml. of tetrahydrofuran was allowed to stand for 52 days at room temperature. The reaction mixture was filtered to remove triethylamine hydrochloride and the filtrate was evaporated to remove solvent. The product was treated with 100 ml. of petroleum ether (b.p. 62°–68° C.) and separated. It was a liquid at room temperature and it was then washed three times by decantation with petroleum ether (b.p. 40°–60° C.). A solution of the product in methylene chloride was charcoaled, filtered and evaporated by heating in a vacuum on a steam bath for a period of two hours. GLC assay showed that the product, 1-[N-butyl-N-(2-ethoxyethyl)carbamoyl]-3-propylsulphonyl-1,2,4-triazole, contained 95.17% of the 1-isomer. Elemental analysis satisfactory.

The N-butyl-N-(2-ethoxyethyl)carbamoyl chloride used in the above reaction was prepared in an analogous way to that described in Example 53.

The 3-propylsulphonyl-1,2,4-triazole used in the above reaction was prepared as follows.

20.2 g. of 3-mercapto-1,2,4-triazole was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue dissolved in ether. The resulting solution was filtered, dried over anhydrous sodium sulphate and distilled under reduced pressure to give 3-propylthio-1,2,4-triazole, b.p. 143°–144° C./1 mm. This product solidified, m.p. 53°–56° C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95°–100° C., kept at this temperature for 2 hours and then distilled to dryness under reduced pressure. The residue was recrystallized from toluene to give 3-propylsulphonyl-1,2,4-triazole, m.p. 116°–117° C. Elemental analysis satisfactory.

The following compounds were prepared in an analogous manner to that described above;

1-[N-ethyl-N-(2-methoxyethyl)carbamyl]-3-isobutylsulphonyl-1,2,4-triazole, an oil (97.3% 1-isomer by GLC assay) $n_D^{23}$ 1.5010

1-[N-ethyl-N-(2-ethoxyethyl)carbamoyl]-3-isobutylsulphonyl-1,2,4-triazole, an oil (90.2% 1-isomer by GLC assay) $n_D^{22}$ 1.4941

1-[N-allyl-N-(2-ethoxyethyl)carbamoyl]-3-ethylsulphonyl-1,2,4-triazole, an oil, $n_D^{22}$ 1.5071

1-[N-allyl-N-(2-ethoxyethyl)carbamoyl]-3-propylsulphonyl-1,2,4-triazole, an oil, $n_D^{22}$ 1.5039

1-[N-allyl-N-(2-ethoxyethyl)carbamoyl]-3-butylsulphonyl-1,2,4-triazole, an oil, $n_D^{22}$ 1.5014

1-[N-butyl-N-(2-ethoxyethyl)carbamoyl]-3-ethylsulphonyl-1,2,4-triazole, an oil (95.2% 1-isomer by GLC assay) $n_D^{22}$ 1.4973

1-[N-butyl-N-(2-ethoxyethyl)carbamoyl]-3-propylsulphonyl-1,2,4-triazole, an oil (96.8% 1-isomer by GLC assay) $n_D^{22}$ 1.4949

1-[N-butyl-N-(2-ethoxyethyl)carbamoyl]-3-butylsulphonyl-1,2,4-triazole, an oil (95.8% 1-isomer by GLC assay) $n_D^{22}$ 1.4930

1-[N-allyl-N-(2-methoxyethyl)carbamoyl]-3-ethylsulphonyl-1,2,4-triazole, an oil, $n_D^{24}$ 1.5112 (93.2% 1-isomer by GLC assay)

1-[N-allyl-N-(2-methoxyethyl)carbamoyl]-3-propylsulphonyl-1,2,4-triazole, an oil, $n_D^{24}$ 1.5075

1-[N-allyl-N-(2-methoxyethyl)carbamoyl]-3-butylsulphonyl-1,2,4-triazole, an oil, $n_D^{24}$ 1.5054

1-[N-allyl-N-(2-methoxyethyl)carbamoyl]-3-(2-ethoxyethylsulphonyl)-1,2,4-triazole, an oil, $n_D^{24}$ 1.5041 (83.3% 1-isomer by GLC assay)

1-[N-butyl-N-(2-methoxyethyl)carbamoyl]-3-ethylsulphonyl-1,2,4-triazole, an oil, $n_D^{19}$ 1.5020 (93.2% 1-isomer by GLC assay)

1-[N-butyl-N-(2-methoxyethyl)carbamoyl]-3-propylsulphonyl-1,2,4-triazole, an oil, $n_D^{19}$ 1.4992 (93.6% 1-isomer by GLC assay)

1-[N-butyl-N-(2-methoxyethyl)carbamoyl]-3-butylsulphonyl-1,2,4-triazole, an oil, $n_D^{19}$ 1.4961 (92.0% 1-isomer by GLC assay)

1-[N-butyl-N-(2-methoxyethyl)carbamoyl]-3-ethoxyethylsulphonyl-1,2,4-triazole, an oil, $n_D^{19}$ 1.4952 (90.6% 1-isomer by GLC assay)

1-[N-ethyl-N-(2-methoxyethyl)carbamoyl]-3-ethoxyethylsulphonyl-1,2,4-triazole, m.p. 51.5°–52.5° C.

1-[N-allyl-N-(3-ethoxypropyl)carbamoyl]-3-ethylsulphonyl-1,2,4-triazole, an oil, $n_D^{21}$ 1.5101 (99.4% 1-isomer by GLC assay)

1-[N-allyl-N-(3-ethoxypropyl)carbamoyl]-3-propylsulphonyl-1,2,4-triazole, an oil, $n_D^{21}$ 1.5070 (94.9% 1-isomer by GLC assay)

1-[N-allyl-N-(3-ethoxypropyl)carbamoyl]-3-butylsulphonyl-1,2,4-triazole, an oil, $n_D^{21}$ 1.5042 (96.4% 1-isomer by GLC assay)

1-[N-ethyl-N-(2-propoxyethyl)carbamoyl]-3-ethylsulphonyl-1,2,4-triazole, an oil, $n_D^{21}$ 1.5010 (97.0% 1-isomer by GLC assay)

1-[N-ethyl-N-(2-propoxyethyl)carbamoyl]-3-propylsulphonyl-1,2,4-triazole, an oil, $n_D^{21}$ 1.4980 (97.4% 1-isomer by GLC assay)

1-[N-ethyl-N-(2-propoxyethyl)carbamoyl]-3-butylsulphonyl-1,2,4-triazole, an oil, $n_D^{21}$ 1.4973 (96.5% 1-isomer by GLC assay)

1-[N-ethyl-N-(2-propoxyethyl)carbamoyl]-3-(2-ethoxyethylsulphonyl)-1,2,4-triazole, an oil, $n_D^{21}$ 1.4966 (95.3% 1-isomer by GLC assay)

1-[N-propyl-N-(2-methoxyethyl)carbamoyl]-3-sec.-butylsulphonyl-1,2,4-triazole, m.p. 55.5°–56.5° C.

1-[N-propyl-N-(2-methoxyethyl)carbamoyl]-3-pentylsulphonyl-1,2,4-triazole, an oil, $n_D^{21}$ 1.4970 (97.8% 1-isomer by GLC assay)

1-[N-propyl-N-(2-methoxyethyl)carbamoyl]-3-(2-methoxyethylsulphonyl)-1,2,4-triazole, an oil, $n_D^{21}$ 1.5021 (95.0% 1-isomer by GLC assay)

1-[N-ethyl-N-(2-ethoxyethyl)carbamoyl]-3-pentylsulphonyl-1,2,4-triazole, an oil, $n_D^{21}$ 1.5002 (92.1% 1-isomer by GLC assay)

1-[N-ethyl-N-(2-ethoxyethyl)carbamoyl]-3-(2-methoxyethylsulphonyl)-1,2,4-triazole, an oil, $n_D^{21}$ 1.4966 (96.5% 1-isomer by GLC assay)

1-[N-propyl-N-(2-methoxyethyl)carbamoyl]-3-(2-ethoxyethylsulphonyl)-1,2,4-triazole, an oil, $n_D^{21}$ 1.5004 (93.9% 1-isomer by GLC assay)

1-[N-propyl-N-(2-ethoxyethyl)carbamoyl]-3-(2-ethoxyethylsulphonyl)-1,2,4-triazole, m.p. 42°–43.5° C.

1-[N-propyl-N-(2-ethoxyethyl)carbamoyl]-3-(2-methoxyethylsulphonyl)-1,2,4-triazole, an oil, $n_D^{22}$ 1.4990 (96.2% 1-isomer by GLC assay)

1-[N-propyl-N-(2-ethoxyethyl)carbamoyl]-3-pentylsulphonyl-1,2,4-triazole, an oil, $n_D^{22}$ 1.4948 (96.7% 1-isomer by GLC assay)

1-[N-ethyl-N-(3-ethoxypropyl)carbamoyl]-3-isopropylsulphonyl-1,2,4-triazole, an oil, $n_D^{23}$ 1.4960 (96.6% 1-isomer by GLC assay).

1-[N-ethyl-N-(3-ethoxypropyl)carbamoyl]-3-butylsulphonyl-1,2,4-triazole, an oil, $n_D^{23}$ 1.4978 (96.5% 1-isomer by GLC assay).

1-[N-ethyl-N-(3-ethoxypropyl)carbamoyl]-3-isobutylsulphonyl-1,2,4-triazole, an oil, $n_D^{25}$ 1.4958 (95.4% 1-isomer by GLC assay).

1-[N-ethyl-N-(3-ethoxypropyl)carbamoyl]-3-pentyl-sulphonyl-1,2,4-triazole, an oil, $n_D^{25}$ 1.4952 (98.3% 1-isomer by GLC assay).

1-[N-ethyl-N-(3-ethoxypropyl)carbamoyl]-3-propyl-sulphonyl-1,2,4-triazole, an oil, $n_D^{23}$ 1.4958 (94.2% 1-isomer by GLC assay).

1-[N-ethyl-N-(2-isopropoxyethyl)carbamoyl]-3-ethylsulphonyl-1,2,4-triazole, an oil, $n_D^{22}$ 1.4983 (98.5% 1-isomer by GLC assay).

1-[N-ethyl-N-(2-isopropoxyethyl)carbamoyl]-3-propylsulphonyl-1,2,4-triazole, an oil, $n_D^{22}$ 1.4958 (97.4% 1-isomer by GLC assay).

1-[N-ethyl-N-(2-isopropoxyethyl)carbamoyl]-3-butylsulphonyl, 1,2,4-triazole, an oil, $n_D^{22}$ 1.4941 (95.9% 1-isomer by GLC assay).

1-[N-ethyl-N-(2-isopropoxyethyl)carbamoyl]-3-(2-ethoxyethylsulphonyl)-1,2,4-triazole, an oil, $n_D^{22}$ 1.4930 (83.8% 1-isomer by GLC assay).

1-[N-ethyl-N-1-methyl-2-propoxyethyl)carbamoyl]-3-propylsulphonyl-1,2,4-triazole, an oil, $n_D^{22}$ 1.4940 (63.8% 1-isomer by GLC assay)

1-[N-ethyl-N-(1-methyl-2-propoxyethyl)carbamoyl]-3-butylsulphonyl-1,2,4-triazole, an oil, $n_D^{22}$ 1.4930 (67.7% 1-isomer by GLC assay)

1-[N-ethyl-N-(3-methoxypropyl)carbamoyl]-3-ethyl-sulphonyl-1,2,4-triazole, an oil, $n_D^{22}$ 1.5021 (96.1% 1-isomer by GLC assay)

1-[N-ethyl-N-(3-methoxypropyl)carbamoyl]-3-propylsulphonyl-1,2,4-triazole, an oil, $n_D^{22}$ 1.4992 (96.8% 1-isomer by GLC assay)

1-[N-ethyl-N-(3-methoxypropyl)carbamoyl]-3-butyl-sulphonyl-1,2,4-triazole, an oil, $n_D^{22}$ 1.4974 (97.8% 1-isomer by GLC assay)

1-[N-ethyl-N-(3-methoxypropyl)carbamoyl]-3-(2-methoxyethylsulphonyl)-1,2,4-triazole, an oil, $n_D^{22}$ 1.5000 (98.0% 1-isomer by GLC assay)

1-[N-propyl-N-methoxymethylcarbamoyl)-3-propyl-sulphonyl-1,2,4-triazole, an oil, $n_D^{26}$ 1.5012 (93.9% 1-isomer by GLC assay)

1-(N-propyl-N-methoxymethylcarbamoyl)-3-sec.-butylsulphonyl-1,2,4-triazole, m.p. 55.5°–56.5° C.

1-(N-methyl-N-methoxymethylcarbamoyl)-3-sec.-butylsulphonyl-1,2,4-triazole, an oil, $n_D^{23}$ 1.5160 (90.1% 1-isomer by GLC assay)

1-[N-ethyl-N-(2-allyloxyethyl)carbamoyl]-3-sec.-butylsulphonyl-1,2,4-triazole, an oil $n_D^{22}$ 1.4983 (97.0% 1-isomer by GLC assay)

1-[N-allyl-N-(2-butoxyethyl)carbamoyl]-3-(2-ethoxy-yethylsulphonyl)-1,2,4-triazole, an oil, $n_D^{21}$ 1.4991 (96.3% 1-isomer by GLC assay).

Satisfactory elemental analyses were obtained for all of the compounds listed above.

The following novel carbamoyl chloride intermediates were prepared. All of these compounds were oils.

N-butyl-N-(2-ethoxyethyl)carbamoyl chloride
N-ethyl-N-(2-ethoxyethyl)carbamoyl chloride
N-allyl-N-(2-ethoxyethyl)carbamoyl chloride
N-allyl-N-(2-methoxyethyl)carbamoyl chloride
N-butyl-N-(2-methoxyethyl)carbamoyl chloride
N-allyl-N-(2-ethoxypropyl)carbamoyl chloride
N-ethyl-N-(2-propoxyethyl)carbamoyl chloride
N-ethyl-N-(2-allyloxyethyl)carbamoyl chloride
N-ethyl-N-(3-ethoxypropyl)carbamoyl chloride
N-ethyl-N-(2-isopropoxyethyl)carbamoyl chloride
N-ethyl-N-(1-methyl-2-propoxyethyl)carbamoyl chloride
N-ethyl-N-(3-methoxypropyl)carbamoyl chloride
N-propyl-N-methoxyethyl carbamoyl chloride
N-methyl-N-methoxymethyl carbamoyl chloride
N-allyl-N-(2-butoxyethyl)carbamoyl chloride
N-propyl-N-(2-methoxyethyl)carbamoyl chloride
N-propyl-N-(2-ethoxyethyl)carbamoyl chloride

EXAMPLE 5

This Example illustrates the preparation of compounds of formula II.

A solution of 7.4 C. 3-(2-allyloxyethylthio)-1,2,4-triazole, 8 ml. triethylamine 6.0 g. diethylcarbamoyl chloride in 40 ml. of tetrahydrofuran was heated under reflux for 15 hours. The cooled reaction mixture was filtered to remove triethylamine hydrochloride and the filtrate was evaporated under vacuum to remove the solvent. Further precipitation of amine hydrochloride was filtered off. The filtrate was dissolved in 50 ml. methylene chloride and washed with ice-cold $^N/10$ sodium hydroxide, with $^N/10$ hydrochloric acid and finally with ice-cold water. The solvent was removed by vacuum distillation to give a liquid product, 1-diethylcarbamoyl-3-(2-allyloxyethylthio)-1,2,4-triazole, b.p. 148°–153° C./0.05 mm. GLC assay showed that the 1-isomer was present to the extent of 98.33%. Elemental analysis was satisfactory.

The novel 3-(2-allyloxyethylthio)-1,2,4-triazole used in the above reaction was made as follows.

To a solution of 2.15 g. sodium in 70 ml. absolute ethanol was added 9.5 g. 1,2,4-triazole-3-thiol and the resulting mixture filtered to remove insoluble materials. After the addition of 18.2 g. 2-allyloxyethylbromide, the mixture was heated under reflux on a steam bath for 5 hours. Solvent was removed by vacuum distillation and the residue extracted with methylene chloride and filtered. The filtrate was distilled so as to remove the methylene chloride and to give an oily product, 3-(2-allyloxyethylthio)-1,2,4-triazole. GLC assay showed that the product was 95.4% pure. Elemental analysis was satisfactory.

The following compound was prepared in an analogous manner to that described above:

1-diallylcarbamoyl-3-(2-allyloxyethylthio)-1,2,4-thiazole, an oil, $n_D^{24}$ 1.5406 (87.6% 1-isomer by GLC assay)

EXAMPLE 6

This Example illustrates the preparation of a compound of formula II.

6.75 g. of 3-(2-methoxyethylsulphinyl)-1,2,4-triazole was dissolved in 40 ml. dry tetrahydrofuran. To this solution was added 8 ml. of triethylamine causing the separation of a lower oily layer. After the addition of 6.75 g. diallyl carbamoyl chloride the mixture was refluxed for 2½ hours. The oil gradually disappeared as triethylamine hydrochloride was precipitated. The mixture was cooled and filtered to remove the triethylamine hydrochloride. After evaporating, the solvent it was found that the residual oil did not crystallize when treated with petroleum ether (b.p. 40°–60° C.). It crystallized at 0° C. but melted again at room temperature. After washing with petrol by decantation the product was taken up in methylene chloride and filtered. Finally the methylene chloride was removed by vacuum distillation to give the liquid product, 1-diallylcarbamoyl-3-(2-methoxyethylsulphinyl)-1,2,4-triazole. The refractive index of the compound, $n_D^{25}$, was 1.5058.

The novel triazole compound used in the above reaction was prepared as follows.

A solution of 31.8 g. of 3-(2-methoxyethylthio)-1,2,4-triazole was dissolved in 300 ml. of acetic acid and heated to 80° C. To this solution was added by portions 67.2 ml. of 100 vol. hydrogen peroxide and the temperature was maintained at 80° C. for two hours with cooling as necessary in the early stages. A small amount of 10% palladium/charcoal catalyst was added to destroy excess hydrogen peroxide. After an hour the solution was filtered and sulphur dioxide passed through the mixture as a precaution in case peroxides had been formed. The solution was vacuum evaporated and crystals of the sulphonyl compound were removed. On the addition of further petroleum ether to the liquors, filtration and vacuum distillation, there was obtained an oily liquid, 3-(2-methoxyethylsulphinyl)-1,2,4-triazole. Elemental analysis satisfactory.

EXAMPLE 7

This Example illustrates the preparation of compounds of formula II.

A solution of 0.03 mole 3-propylsulphonyl-1,2,4-triazole, 10 ml. triethylamine, 0.03 mole N-propyl-N-(2-chloroallyl)carbamoyl chloride in 40 ml. of dry tetrahydrofuran was refluxed for 15 hours. The mixture was then cooled and the triethylamine hydrochloride filtered off. After removal of the solvent the product was dissolved in methylene chloride and the solution washed with water. The product was recrystallized from an ether/petroleum ether (b.p. 40°-60° C.) mixture. It was 1-[N-propyl-N-(2-chloroallyl)carbamoyl]-3-propylsulphonyl-1,2,4-triazole, m.p. 51.5°-52° C. Elemental analysis was satisfactory.

The novel carbamoyl chloride used in the above reaction was prepared as follows:

80 g. of sodium hydroxide pellets were dissolved in 350 ml. water in a stirred two liter flask. The solution was cooled and 295 g. propylamine was added. The temperature was adjusted to 40° C. and maintained at this level whilst 222 g. of 2,3-dichloropropene was added over a period of about two hours. Heat evolution was observed. After stirring for a further two hours at 40° C., the mixture was gradually brought to reflux on the steam bath. It was refluxed gently for two hours and then allowed to stand for 15 hours at ambient temperature. Excess polyamine was distilled off through a 40 cm. bead-packed column. After cooling, the upper amine layer was separated and run with stirring into a cooled solution of concentrated hydrochloric acid in water.

The aqueous layer was extracted with ether and the extract stirred for ten minutes with the hydrochloric acid solution. The ether was separated and discarded and the aqueous solution was evaporated in vacuo on the steam bath. Water was added, the solution was cooled in ice and 200 ml. of 18.5 N sodium hydroxide added. The amine layer was separated, dried over successive amounts of sodium hydroxide pellets and distilled from an oil bath through a bead-packed column. The product, N-(2-chloroallyl)propylamine, had a b.p. of 148°-153° C.

250 ml. ethyl acetate was stirred and heated under reflux whilst a brisk stream of phosgene was passed in. A solution of 0.25 mole. N-(2-chloroallyl)propylamine in 75 ml. ethyl acetate was then added dropwise over a period of about 4½ hours. After passing in phosgene for a further fifteen minutes, ethyl acetate was removed in vacuo and the product vacuum distilled; N-propyl-N-(2-chloroallyl) carbamoyl chloride, b.p. 97°-99° C./17 mm.

The triazole intermediate used in the preparation was made as follows.

3-Mercapto-1,2,4-triazole (20.2 g.) was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue was dissolved in ether. The resulting solution was filtered, dried over anhydrous sodium sulphate and distilled under reduced pressure to give 3-propylthio-1,2,4 triazole, b.p. 143°-144° C./1 mm. This product solidified, m.p. 53°-56° C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95°-100° C., kept at this temperature for 2 hours and then distilled to dryness under reduced pressure. The residue was recrystallized from toluene to give 3-propylsulphonyl-1,2,4-triazole, m.p. 116°-117° C. Elemental analysis satisfactory.

The following compounds were produced by an analogous method:

1-[N-propyl-N-(2-chloroethyl)carbamoyl]-3-methylsulphonyl-1,2,4-triazole, m.p. 106.5°-107° C.

1-[N-propyl-N-(2-chloroallyl)carbamoyl]-3-sec.-butylsulphonyl-1,2,4-triazole, an oil, $n_D^{25}$ 1.5178.

1-[N-ethyl-N-(2-chloroallyl)carbamoyl]-3-isopropylsulphonyl-1,2,4-triazole, m.p. 75.5°-76.5° C.

1-[N-ethyl-N-(2-chloroallyl)carbamoyl]-3-butylsulphonyl-1,2,4-triazole, an oil $n_D^{22}$ 1.5198 (97.1% 1-isomer by GLC assay)

1-[N-ethyl-N-(2-chloroallyl)carbamoyl]-3-isobutylsulphonyl-1,2,4-triazole, an oil, $n_D^{22}$ 1.5195 (97.9% 1-isomer by GLC assay)

1-[N-ethyl-N-(2-chloroallyl)carbamoyl]-3-sec.butylsulphonyl-1,2,4-triazole, an oil, $n_D^{22}$ 1.5231 (98.1% 1-isomer by GLC assay)

1-[N-ethyl-N-(2-chloroallyl)carbamoyl]-3-ethylsulphonyl-1,2,4-triazole, an oil, $n_D^{22}$ 1.5298 (96.4% 1-isomer by GLC assay)

1-[N-ethyl-N-(2-chloroallyl)carbamoyl]-3-propylsulphonyl-1,2,4-triazole, an oil, $n_D^{22}$ 1.5243 (97.2% 1-isomer by GLC assay)

1-[N-allyl-N-(2-chloroallyl)carbamoyl]-3-ethylsulphonyl-1,2,4-triazole, an oil, $n_D^{26}$ 1.5306

1-[N-allyl-N-(2-chloroallyl)carbamoyl]-3-propylsulphonyl-1,2,4-triazole, an oil, $n_D^{26}$ 1.5260

1-[N-allyl-N-(2-chloroallyl)carbamoyl]-3-isopropylsulphonyl-1,2,4-triazole, an oil, $n_D^{26}$ 1.5274

1-[N-allyl-N-(2-chloroallyl)carbamoyl]-3-butylsulphonyl-1,2,4-triazole, an oil, $n_D^{26}$ 1.5220 (94.9% 1-isomer by GLC assay)

1-[N-allyl-N-(2-chloroallyl)carbamoyl]-3-isobutylsulphonyl-1,2,4-triazole, an oil, $n_D^{26}$ 1.5214 (94.8% 1-isomer by GLC assay)

1-[N-allyl-N-(2-chloroallyl)carbamoyl]-3-sec.butylsulphonyl-1,2,4-triazole, an oil, $n_D^{26}$ 1.5248 (95.3% 1-isomer by GLC assay)

The following novel intermediate carbamoyl chloride was prepared:

N-ethyl-N-(2-chloroallyl)carbamoyl chloride, b.p. 62.5°-66° C./0.1 mm. (98.9% 1-isomer by GLC assay)

EXAMPLE 8

This Example illustrates the preparation of compounds of the formula II.

A solution of 6.15 g. 3-(2-ethoxyethylsulphonyl)-1,2,4-triazole, 6 ml. triethylamine, 7.15 g N-ethyl-N-(2,3-dichloroallyl)carbamoyl chloride in 40 ml. of dry tetrahydrofuran was heated under reflux for six hours. After cooling the amine hydrochloride was filtered off. The solvent was removed and the product solidified on cooling. It was crystallized from benzene/petroleum ether (b.p. 62°–68° C.) mixture and was found to have a m.p. of 82°–83.5° C. The product was 1-[N-ethyl-N-(2,3-dichloroallyl)carbamoyl]-3-(2-ethoxyethylsulphonyl)-1,2,4-triazole. Elemental analysis was satisfactory.

The triazole and carbamoyl chloride intermediates were prepared a similar way to that described in Example 58.

The following compounds were prepared in an analogous way:

1-[N-ethyl-N-(2-chloroallyl)carbamoyl]-3-(2-methoxyethylsulphonyl)-1,2,4-triazole, m.p. 52°–53° C.
1-[N-ethyl-N-(2-chloroallyl)carbamoyl]-3-(2-ethoxyethylsulphonyl)1,2,4-triazole, m.p. 79.5°–80° C.
1-[N-propyl-N-chloroallyl)carbamoyl]-3-(2-methoxyethylsulphonyl)-1,2,4-triazole, m.p. 58°–60° C.
1-[N-propyl-N-(2-chloroallyl)carbamoyl]-3-(2-ethoxyethylsulphonyl)-1,2,4-triazole, m.p. 47°–49° C.
1-(N-ethyl-N-chloromethylcarbamoyl)-3-(2-ethoxyethylsulphonyl)-1,2,4-triazole, m.p. 71°–72° C.
1-[N-allyl-N-(2-chloroallyl)carbamoyl]-3-(2-methoxyethylsulphonyl)-1,2,4-triazole, an oil, $n_D^{26}$ 1.5256 (93.4% 1-isomer by GLC)
1-[N-allyl-N-(2-chloroallyl)carbamoyl]-3-(2-ethoxyethylsulphonyl-1,2,4-triazole, m.p. 71°–80° C.

EXAMPLE 9

This Example illustrates the preparation of a compound of formula II.

A solution of 7.5 g. 1-dipropylcarbamoyl-3-butylsulphinyl-1,2,4-triazole and 4 ml. dry pyridine in 15 ml. of methylene chloride was cooled in ice and stirred whilst a solution of 2 ml. sulphuryl chloride in 10 ml. methylene chloride was slowly added. Stirring in the ice-bath was continued for one hour, followed by stirring at ambient temperature for a further hour. The solution was rapidly washed with ice-cold water, dried over magnesium sulphate and the solvent removed in vacuo. The product, 1-dipropylcarbamoyl-3-(1-chlorobutylsulphinyl)-1,2,4-triazole was a viscous gum which did not crystallize even when cooled in solid carbon dioxide-/acetone. Elemental analysis was satisfactory.

EXAMPLE 10

In an analogous manner to that described in Example 6, the following compounds were prepared.

1-[N-propyl-N-(2-chloroallyl)carbamoyl]-3-n-butylsulphonyl-1,2,4-triazole, an oil, $n_D^{25}$ 1.5136
1-[N-propyl-N-(2-choroally)carbamoyl]-3-ethylsulphonyl-1,2,4-triazole, m.p. 50°–50.5° C.
1-[N-propyl-N-(2-chloroallyl)carbamoyl]-3-isobutylsulphonyl-1,2,4-triazole, an oil, $n_D^{25}$ 1.5125
1-[N-propyl-N-(2-chloroallyl)carbamoyl]-3-isopropylsulphonyl-1,2,4-triazole, an oil, $n_D^{25}$ 1.5168
1-[N-ethyl-N-(2-chloroethyl)carbamoyl]-3-ethylsulphonyl-1,2,4-triazole, m.p. 73°–74° C.
1-[N-propyl-N-(2-chloroethyl)carbamoyl]-3-ethylsulphonyl-1,2,4-triazole, m.p. 55°–56° C.

The following novel intermediate carbamoyl chlorides were prepared.
N-ethyl-N-(2-chloroethyl)carbamoyl chloride
N-propyl-N-(2-chloroethyl)carbamoyl chloride

EXAMPLE 11

This Example illustrates the preparation of compounds of formula II.

A solution of 0.03 mole 3-propylsulphonyl-1,2,4-triazole, 6 ml. triethylamine and 0.033 mole N-ethyl-N-cyclopropylcarbamoyl chloride in 40 ml. dry tetrahydrofuran was heated under reflux for 5 hours. The cooled reaction mixture was filtered to remove triethylamine hydrochloride and the filtrate was evaporated to remove solvent. An ether solution of the liquid product was charcoaled, the ether evaporated and the residue heated to 120° C. in a high vacuum to remove excess carbamoyl chloride, 1-(N-ethyl-N-cyclopropylcarbamoyl)-3-propylsulphonyl-1,2,4-triazole $n_D^{22}$ 1.5148 (96.6% 1-isomer by GLC assay). Elemental analysis was satisfactory.

The novel carbamoyl chloride used in the above reaction was prepared as follows.

First the novel N-ethyl-N-cyclopropylamine was prepared. 28.5 g. cyclopropylamine was diluted with 75 ml. absolute ethanol and cooled below 20° C. whilst 19.8 g. acetaldehyde was added over a period of fifteen minutes. The solution was added to 75 ml. absolute ethanol in which 0.3 g. of platinum oxide had been reduced at ambient temperature and pressure. The solution was added and hydrogenated likewise and the theoretical amount of hydrogen was absorbed in about five hours. After separation from the catalyst by decantation, the solution was made definitely acid by the addition of 50 ml. of concentrated hydrochloric acid and evaporated in vacuo on a steam bath. The residue was dissolved in 70 ml. water and the amine liberated by the addition of 50 ml. of 18.5 N sodium hydroxide.

The amine layer was separated and dried over successive amounts of sodium hydroxide pellets. It was distilled from barium oxide to give a liquid product, b.p. 82°–85° C.

250 ml. of ethyl acetate was stirred and refluxed whilst a brisk stream of phosgene was passed in. After about ten minutes a solution of 21.95 g. cyclopropylamine in 75 ml. ethyl acetate was added dropwise below the surface of the liquid over a period of 2½ hours. After a further fifteen minutes the ethyl acetate was distilled off and the residual oil distilled in vacuo, b.p. 96° C./17 mm.

The following compunds were prepared in an analogous way:

1-(N-ethyl-N-cyclopropylcarbamoyl)-3-butylsulphonyl-1,2,4-triazole, m.p. 68°–68.5° C.
1-(N-ethyl-N-cyclopropylcarbamoyl)-3-isopropylsulphonyl-1,2,4-triazole, m.p. 51°–52° C.
1-(N-ethyl-N-cyclopropylcarbamoyl)-3-ethylsulphonyl-1,2,4-triazole, an oil, $n_D^{15}$ 1.5214 (94.7% 1-isomer by GLC assay)
1-(N-propyl-N-cyclopropylcarbamoyl)-3-ethylnulphonyl-1,2,4-triazole, an oil, $n_D^{22}$ 1.5147 (94.5% 1-isomer by GLC assay)
1-(N-propyl-N-cyclopropylcarbamoyl)-3-propylsulphonyl-1,2,4-triazole, an oil, $n_D^{22}$ 1.5100 (95.1% 1-isomer by GLC assay)

1-(N-propyl-N-cyclopropylcarbamoyl)-3-isopropyl-sulphonyl-1,2,4-triazole, an oil, $n_D^{22}$ 1.5114 (98.4% 1-isomer by GLC assay)

1-(N-propyl-N-cyclopropylcarbamoyl)-3-butylsulphonyl-1,2,4-triazole, an oil, $n_D^{22}$ 1.5079 (97.3% 1-isomer by GLC assay)

The following novel intermediates were prepared.

N-propyl-N-cyclopropylamine, b.p. 108°–110° C.

N-propyl-N-cyclopropylcarbamoyl chloride, b.p. 112°–114° C./20 mm.

EXAMPLE 12

This Example illustrates the preparation of compounds of formula II.

A solution of 6.15 g. 3-(2-ethoxyethylsulphonyl)-1,2,4-triazole, 6 ml. triethylamine and 4.9 g. N-ethyl-N-cyclopropylcarbamoyl chloride in 40 ml. of dry tetrahydrofuran was heated under reflux for 15 hours. The cooled reaction mixture was filtered to remove triethylamine hydrochloride and the filtrate was evaporated to remove solvent. The product was treated with 100 ml. petrol (b.p. 62°–68° C.) and stirred. Crystals were collected and recrystallized from benzene/petrol (b.p. 62°–68° C.) mixture. 1-N-ethyl-N-cyclopropylcarbamoyl-3-(2-ethoxyethylsulphonyl)-1,2,4-triazole was found to have a melting point of 89.5°–90.5° C. Elemental analysis was satisfactory.

EXAMPLE 13

This Example illustrates the preparation of a composition comprising a compound of the formula II.

A dispersible powder was prepared by grinding together a mixture of the following ingredients in a hammer mill.

|  | %w/w |
|---|---|
| 1-Diallylcarbamoyl-3-(2-ethoxyethylsulphonyl)-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared in which the triazole compound in the above formulation was replaced by the following compounds.

1-Diallylcarbamoyl-3-(2-methoxyethylsulphonyl)-1,2,4-triazole

1-Dipropylcarbamoyl-3-(2-ethoxyethylsulphonyl)-1,2,4-triazole

EXAMPLE 14

This Example illustrates the preparation of a composition comprising a compound of the formula II.

An emulsifiable concentrate suitable for dilution with water to form an aqueous emulsion was prepared from the following ingredients.

|  | %w/v |
|---|---|
| 1-(N-ethyl-N-2-methoxyethylcarbamoyl)-3-ethylsulphonyl-1,2,4-triazole | 20.0 |
| Calcium dodecylbenzenesulphonate | 2.5 |
| Nonylphenoxypolyethoxyethanol* | 2.5 |
| Xylene | to 100.0 |

A nonylphenol-ethylene oxide condensate containing an average of 14 mols. ethylene oxide per mol. nonylphenol.

Similar emulsifiable concentrates were prepared in which the triazole compound in the above formulation was replaced by the following compounds.

1-(N-ethyl-N-2-ethoxyethylcarbamoyl)-3-n-butylsulphonyl-1,2,4-triazole 1-(N-ethyl-N-2-ethoxyethylcarbamoyl)-3-isobutylsulphonyl-1,2,4-triazole 1-(N-propyl-N-2-methoxyethylcarbamoyl)-3-n-butylsulphonyl-1,2,4-triazole.

EXAMPLE 15

This Example illustrates the herbicidal use of a composition comprising a compound of the formula II.

In tests carried out in the glasshouse, trays of soil were sown with seeds of various weeds and then immediately sprayed with aqueous suspensions of compounds under test at various application rates of test compound. Seeded trays of soil receiving no chemical treatment were used as controls. At an application rate of 0.5 lb./acre, all the triazoles mentioned in Examples 13 and 14 controlled the weeds crabgrass, barnyard grass, yellow foxtail and Johnson grass (no germination or emergent seedlings severely and irrecoverably stunted).

EXAMPLE 16

This Example illustrates the use of herbicidal compositions comprising a compound of the formula II Compositions were prepared containing the following compounds as active ingredients:

1-(N-propyl-N-prop-2-ynylcarbamoyl)-3-(2-ethoxyethyl-sulphonyl)-1,2,4-triazole.

1-[N-butyl-N-(2-methoxyethyl)carbamoyl]-3-propylsulphonyl-1,2,4-triazole.

1-[N-allyl-N-(2-ethoxyethyl)carbamoyl]-3-butylsulphonyl-1,2,4-triazole.

1-(N-butyl-N-ethylcarbamoyl)-3-(2-ethoxyethylsulphonyl)-1,2,4-triazole.

1-(N-cyclopropyl-N-propylcarbamoyl)-3-butylsulphonyl-1,2,4-triazole.

Rice seedlings were grown under paddy conditions in the glasshouse. At the 2–3 leaf stage the trays containing the seedlings were seeded with barnyard grass and then sprayed with aqueous emulsions prepared from the above concentrates, at an application rate of active ingredient of ⅛ lb./acre. After seven days the trays were flooded with water and examined 21 days after spraying.

No barnyard grass was observed in the trays sprayed with the aqueous emulsions described above, and no lasting phytotoxic effect on the rice plants was observed. A growth of barnyard grass had occurred in control trays that had received no chemical treatment.

We claim:

1. A compound of the general formula

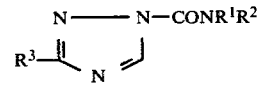

in which $R^3$ is alkylsulphonyl containing 1–5 carbon atoms, alkenyloxyalkylthio containing 4–6 carbon atoms, alkoxyalkylsulphinyl containing 2–6 carbon atoms, alkoxyalkylsulphonyl containing 2–6 carbon atoms, haloalkylsulphinyl containing 2–5 carbon atoms or haloalkylsulphonyl containing 1-5 carbon atoms, $R^1$ is alkyl containing 2-6 carbon atoms, allyl, 2-methylallyl, alkoxyalkyl containing 2-6 carbon atoms, alkenyloxyalkyl containing 4-6 carbon atoms, haloalkyl containing 2-6 carbon atoms, 2-haloallyl or 2,3-dihaloallyl, and $R^2$ is alkyl containing 2-3 carbon atoms, allyl, 2-methylallyl, prop-2-ynyl, alkoxyalkyl containing 2-4 carbon atoms, haloalkyl containing 2-3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

2. A compound according to claim 1 in which $R^3$ is alkylsulphonyl containing 1-4 carbon atoms or alkoxyalkylsulphonyl containing 2-6 carbon atoms, $R^1$ is alkyl containing 2-6 carbon atoms, allyl, 2-methylallyl, alkoxyalkyl containing 2-6 carbon atoms, alkenyloxyalkyl containing 4-6 carbon atoms, haloalkyl containing 2-6 carbon atoms, 2-haloallyl or 2,3-dihaloallyl and $R^2$ is alkyl containing 2-3 carbon atoms, allyl, 2-methylallyl, prop-2-ynyl, alkoxyalkyl containing 2-4 carbon atoms, haloalkyl containing 2-3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

3. A compound according to claim 2 in which $R^3$ is alkylsulphonyl containing 1-4 carbon atoms or alkoxyalkylsulphonyl containing 3-6 carbon atoms, $R^1$ is alkyl containing 2-6 carbon atoms, allyl, alkoxyalkyl containing 3-6 carbon atoms, alkenyloxyalkyl containing 5-6 carbon atoms, haloalkyl containing 2-6 carbon atoms, 2-haloallyl or 2,3-dihaloallyl and $R^2$ is alkyl containing 2-3 carbon atoms, allyl, 2-methylallyl, prop-2-ynyl, alkoxyalkyl containing 3-4 carbon atoms, haloalkyl containing 2-3 carbon atoms, 2,3-dihaloallyl or cyclopropyl, provided that at least one of the groups $R^1$, $R^2$ and $R^3$ contains an alkoxy substituent.

4. A compound according to claim 3 in which $R^1$ is alkyl containing 2-6 carbon atoms, allyl, alkoxyalkyl containing 3-5 carbon atoms, 2-haloallyl and $R^2$ is alkyl containing 2-3 carbon atoms, allyl, 2-methylallyl, prop-2-ynyl or cyclopropyl.

5. A compound according to claim 4 in which $R^3$ is alkylsulphonyl containing 2-4 carbon atoms or alkoxyalkylsulphonyl containing 3-5 carbon atoms.

6. A compound according to claim 1 in which $R^3$ is alkylsulphonyl containing 2-6 carbon atoms and the carbamoyl group $CONR^1R^2$ is N-alkyl-N-alkoxyalkylcarbamoyl or N-allyl-N-alkoxyalkylcarbamoyl.

7. A compound according to claim 1 in which $R^3$ is alkoxyalkylsulphonyl containing 3-5 carbon atoms and the carbamoyl group $CONR^1R^2$ is N-diallylcarbamoyl, N-alkyl-N-allylcarbamoyl, N-alkyl-N-propynylcarbamoyl or N-dialkylcarbamoyl.

8. A compound according to claim 1 in which $R^3$ is alkylsulphenyl containing 2-3 carbon atoms or alkoxyalkylsulphonyl containing 3-5 carbon atoms and the carbamoyl group $CONR^1R^2$ is N-alkyl-N-(2-haloallyl)-carbamoyl.

9. A compound according to claim 1 in which $R^3$ is alkylsulphonyl containing 2-4 carbon atoms or alkoxyalkylsulphonyl containing 3-5 carbon atoms and the carbamoyl group $CONR^1R^2$ is N-cyclopropyl-N-alkylcarbamoyl in which the alkyl group contains 2-4 carbon atoms.

10. A herbicidal composition which comprises as an active ingredient a herbicidally effective amount of a triazole of the general formula defined in claim 1 in association with a diluent or carrier.

11. A herbicidal composition which comprises as an active ingredient a herbicidally effective amount of a triazole of the general formula defined in claim 2 in association with a diluent or carrier.

12. A method for the pre-weed emergence control of graminaceous weeds which comprises applying to the locus of the weeds a herbicidally effective amount of a triazole of the general formula

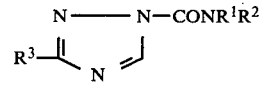

in which $R^3$ is alkylsulphonyl containing 1-5 carbon atoms, alkenyloxyalkylthio containing 4-6 carbon atoms, alkoxyalkylsulphinyl containing 2-6 carbon atoms, alkoxyalkylsulphonyl containing 2-6 carbon atoms, haloalkylsulphinyl containing 2-5 carbon atoms or haloalkylsulphonyl containing 1-5 carbon atoms, $R^1$ is alkyl containing 2-6 carbon atoms, allyl, 2-methylallyl, alkoxyalkyl containing 2-6 carbon atoms, alkenyloxyalkyl containing 4-6 carbon atoms, haloalkyl containing 2-6 carbon atoms, 2-haloallyl or 2,3-dihaloallyl, and $R^2$ is alkyl containing 2-3 carbon atoms, allyl, 2-methylallyl, prop-2-ynyl, alkoxyalkyl containing 2-4 carbon atoms, haloalkyl containing 2-3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

13. A method for the pre-weed emergence control of graminaceous weeds which comprises applying to the locus of the weeds a herbicidally effective amount of a triazole of the general formula defined in claim 2 in which $R^3$ is alkylsulphonyl containing 1-4 carbon atoms or alkoxyalkylsulphonyl containing 2-6 carbon atoms, $R^1$ is alkyl containing 2-6 carbon atoms, allyl, 2-methylallyl, alkoxyalkyl containing 2-6 carbon atoms, alkenyloxyalkyl containing 4-6 carbon atoms, haloalkyl containing 2-6 carbon atoms, 2-haloallyl or 2,3-dihaloallyl and $R^2$ is alkyl containing 2-3 carbon atoms, allyl, 2-methylallyl, prop-2-ynyl, alkoxyalkyl containing 2-4 carbon atoms, haloalkyl containing 2-3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents.

14. A method according to claim 13 for selectively controlling graminaceous weeds in a crop area in which the triazole is applied to a crop area at an application rate sufficient to control the weeds but substantially non-phototoxic to the crop.

15. A method according to claim 14 in which the weeds crabgrass, barnyard grass, yellow foxtail, and Johnson grass are controlled in a crop area selected from cotton, soyabean, maize and peanut.

16. A method according to claim 15 in which the crop area is selected from cotton, soyabean and peanut.

* * * * *